US010307247B2

(12) United States Patent
McCafferty

(10) Patent No.: US 10,307,247 B2
(45) Date of Patent: Jun. 4, 2019

(54) REFOCUSABLE LENS SYSTEM WITH MUTUALLY-APPLANATING INTERNAL SURFACES

(71) Applicant: Conexus Lens, Inc., Tucson, AZ (US)

(72) Inventor: Sean J. McCafferty, Tucson, AZ (US)

(73) Assignee: Conexus Lens, Inc., Tucson, AZ (US)

( * ) Notice: Subject to any disclaimer, the term of this patent is extended or adjusted under 35 U.S.C. 154(b) by 0 days.

(21) Appl. No.: 15/814,168

(22) Filed: Nov. 15, 2017

(65) Prior Publication Data

US 2018/0071082 A1 Mar. 15, 2018

Related U.S. Application Data

(60) Division of application No. 15/258,119, filed on Sep. 7, 2016, now Pat. No. 9,848,980, which is a
(Continued)

(51) Int. Cl.
*A61F 2/16* (2006.01)
(52) U.S. Cl.
CPC .......... *A61F 2/1629* (2013.01); *A61F 2/1602* (2013.01); *A61F 2/1635* (2013.01);
(Continued)
(58) Field of Classification Search
None
See application file for complete search history.

(56) References Cited

U.S. PATENT DOCUMENTS 661,691 A 11/1900 Goodwin
5,489,302 A 2/1996 Scottun
(Continued)

FOREIGN PATENT DOCUMENTS

WO WO 01/08605 * 2/2001 ............... A61F 2/16

OTHER PUBLICATIONS

Extended European Search Report issued in related European Application 14884763.5, dated Dec. 22, 2017, 7 pages.

*Primary Examiner* — Leslie Lopez
(74) *Attorney, Agent, or Firm* — Yakov S. Sidorin; Quarles & Brady LLP

(57) ABSTRACT

An accommodating (re-focusable) lens system a body of which includes, upon being assembled, first and second individual lenslets having first and second optical portions sequentially disposed along an optical axis. Change in optical-power accommodation of the system is achieved by changing an applanated area of contact between the lenslets in response to force applied to the lenslets and transformed into an axial force. In specific case, the first and second lenslets form an intraocular lens (IOL) and have respective haptic portions, interlocked as a result of rotating of one lenslet with respect to another such as to bring first and second lenslets in contact at an axial point. The applanated area of contact is changed, then, in response to a radially-directed force caused by a change of distance between the interlocked ends of the haptics and transferred to the optical portions through the interlocked haptics. When installed in a natural lens capsule after the cataract extraction, the optical power of such IOL is gradually modifiable due to a change of curvature of the capsule caused by operation of a ciliary muscle.

13 Claims, 16 Drawing Sheets

Related U.S. Application Data continuation of application No. PCT/US2014/050318, filed on Aug. 8, 2014, and a continuation-in-part of application No. 14/334,514, filed on Jul. 17, 2014, now abandoned.

(60) Provisional application No. 61/949,268, filed on Mar. 7, 2014.

(52) U.S. Cl.
CPC .......... *A61F 2/1648* (2013.01); *A61F 2/1651* (2015.04); *A61F 2002/1682* (2015.04); *A61F 2220/0033* (2013.01)

(56) References Cited

U.S. PATENT DOCUMENTS

| | | | |
|---|---|---|---|
| 2001/0007075 A1 | 7/2001 | Hjertman et al. | |
| 2002/0105617 A1* | 8/2002 | Norrby | A61B 3/0025 351/159.74 |
| 2002/0107568 A1* | 8/2002 | Zadno-Azizi | A61F 2/1629 623/6.37 |
| 2004/0236422 A1 | 11/2004 | Zhang et al. | |
| 2007/0078515 A1 | 4/2007 | Brady | |
| 2009/0125106 A1* | 5/2009 | Weinschenk, III | A61F 2/1613 623/6.32 |
| 2009/0234448 A1 | 9/2009 | Weeber et al. | |
| 2010/0016964 A1* | 1/2010 | Werblin | A61F 2/1648 623/6.34 |
| 2011/0040378 A1 | 2/2011 | Werblin | |

\* cited by examiner

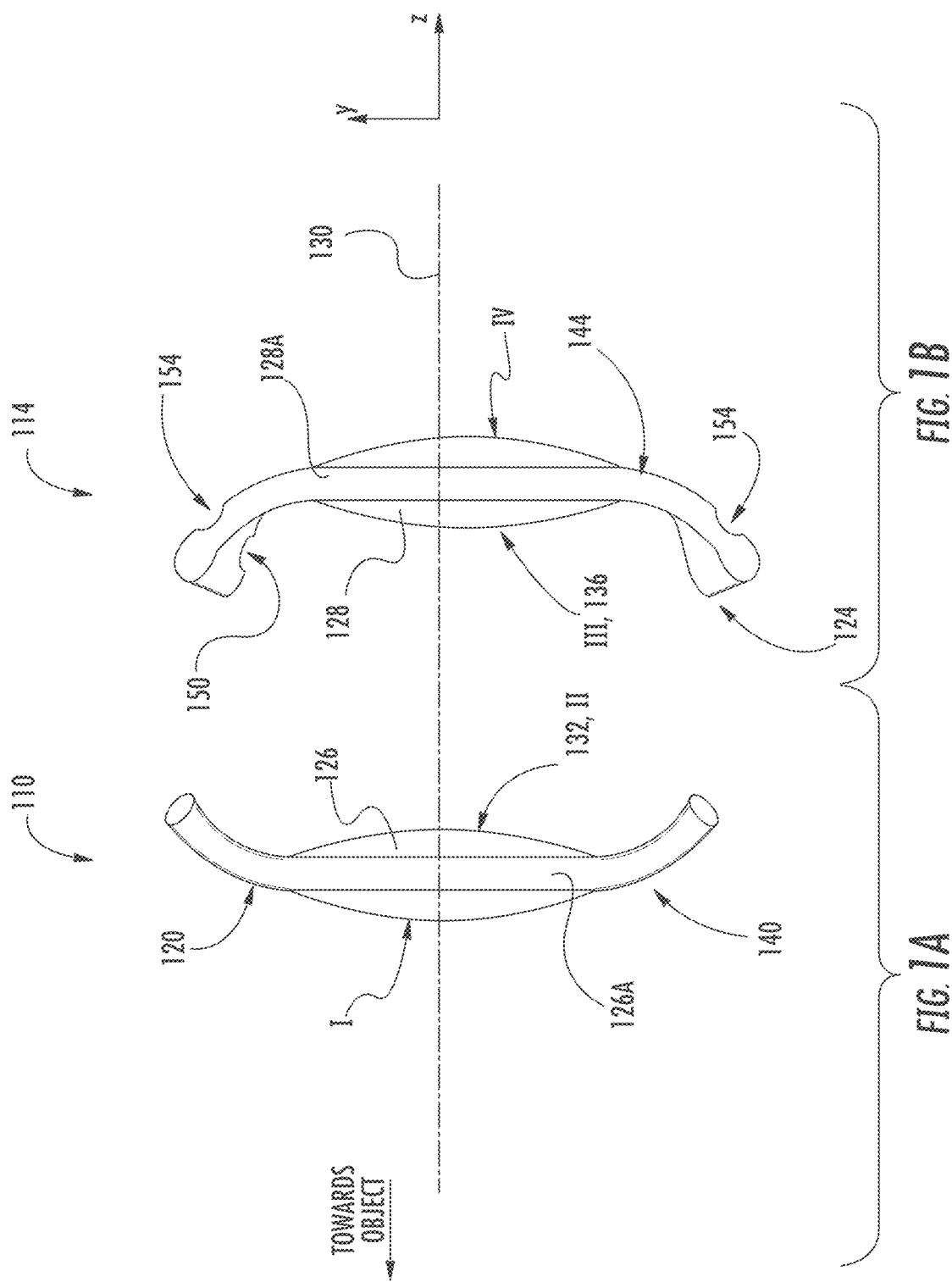

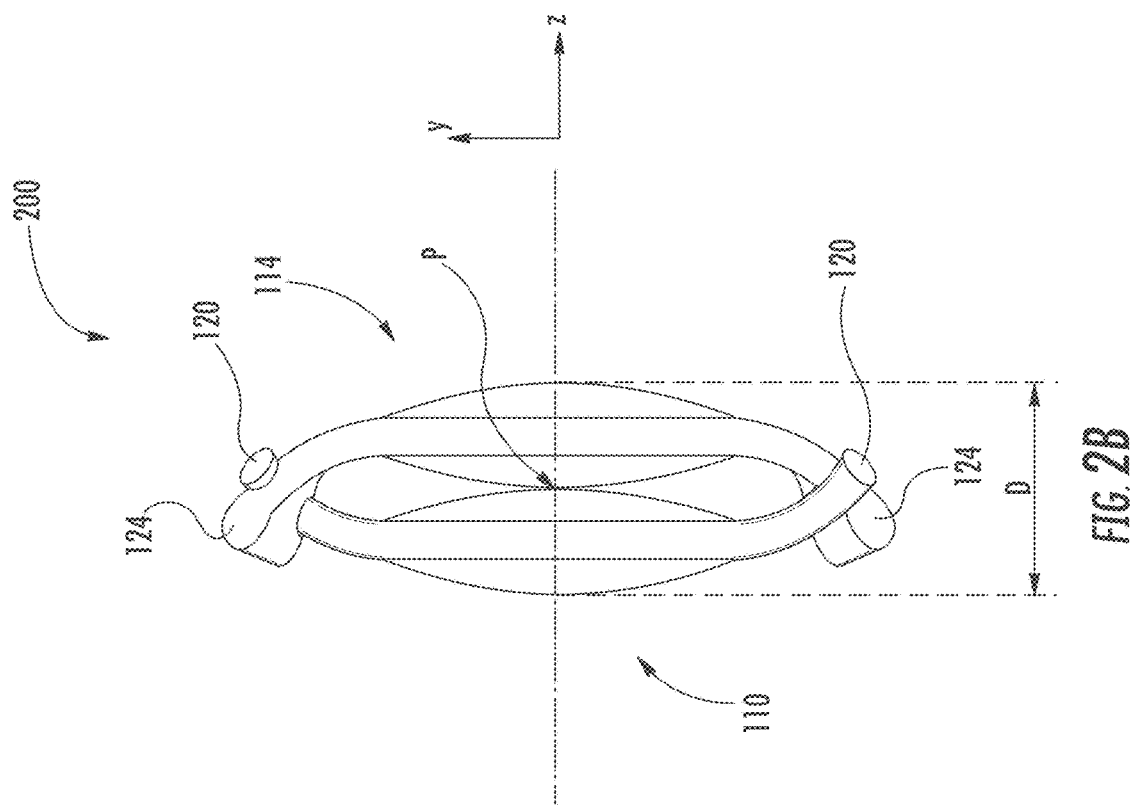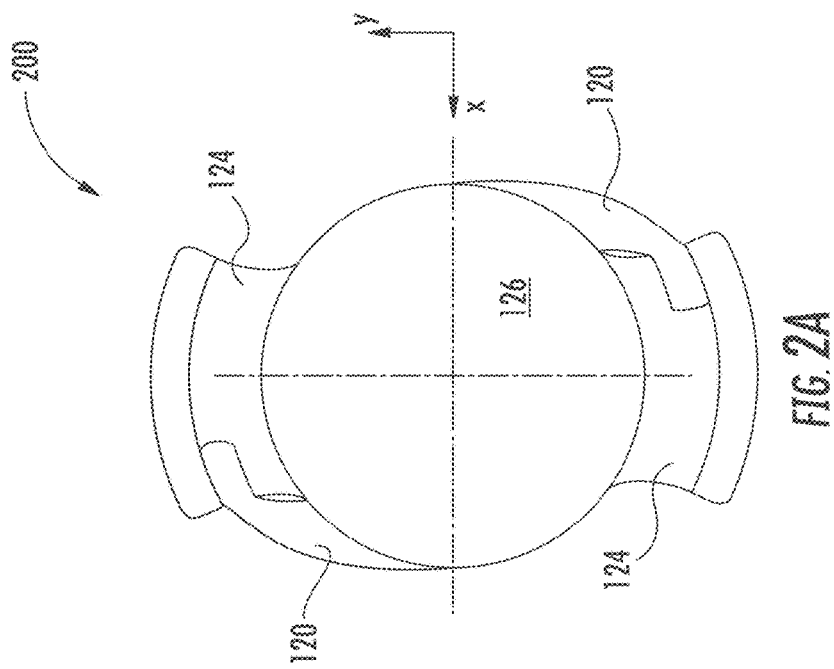

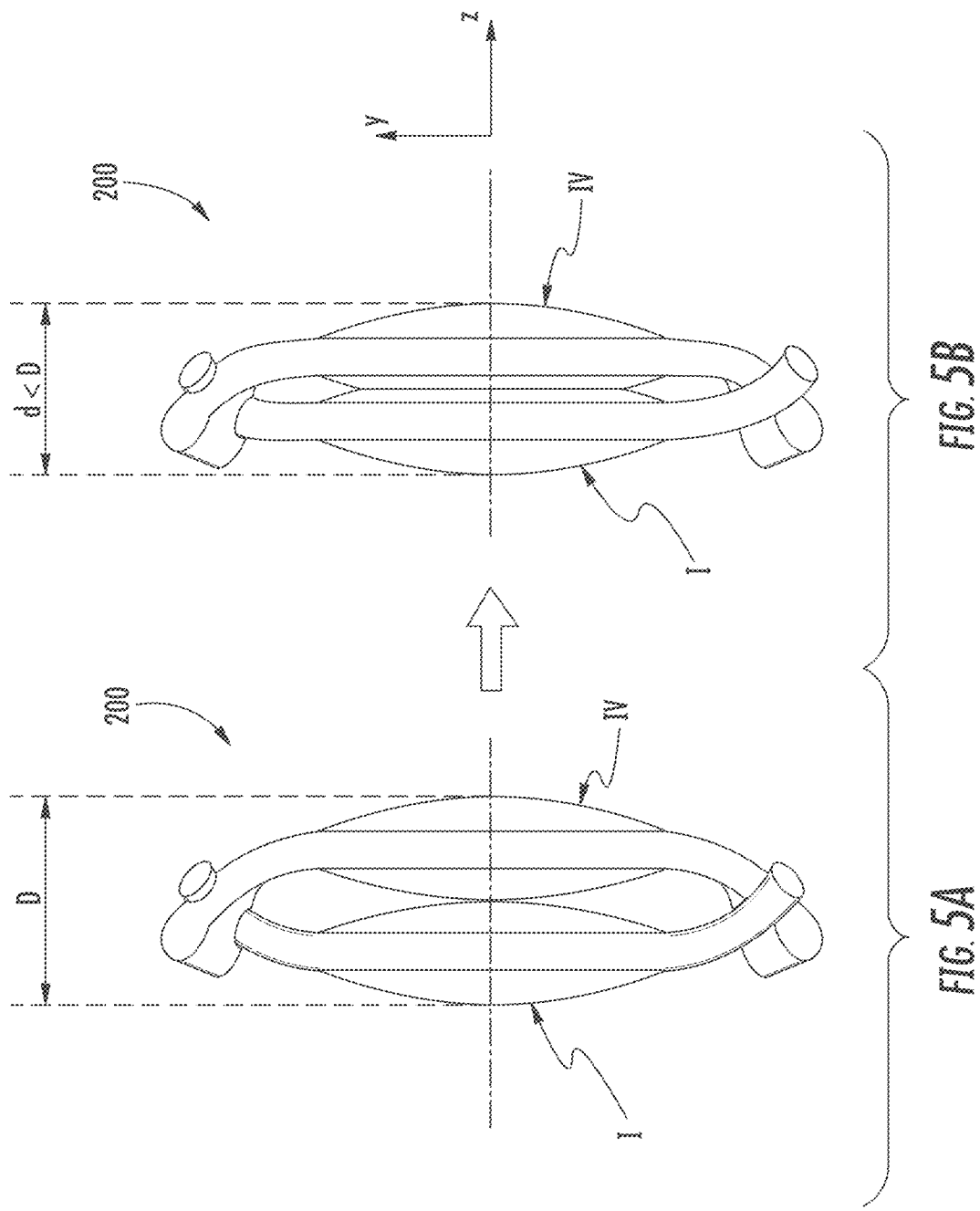

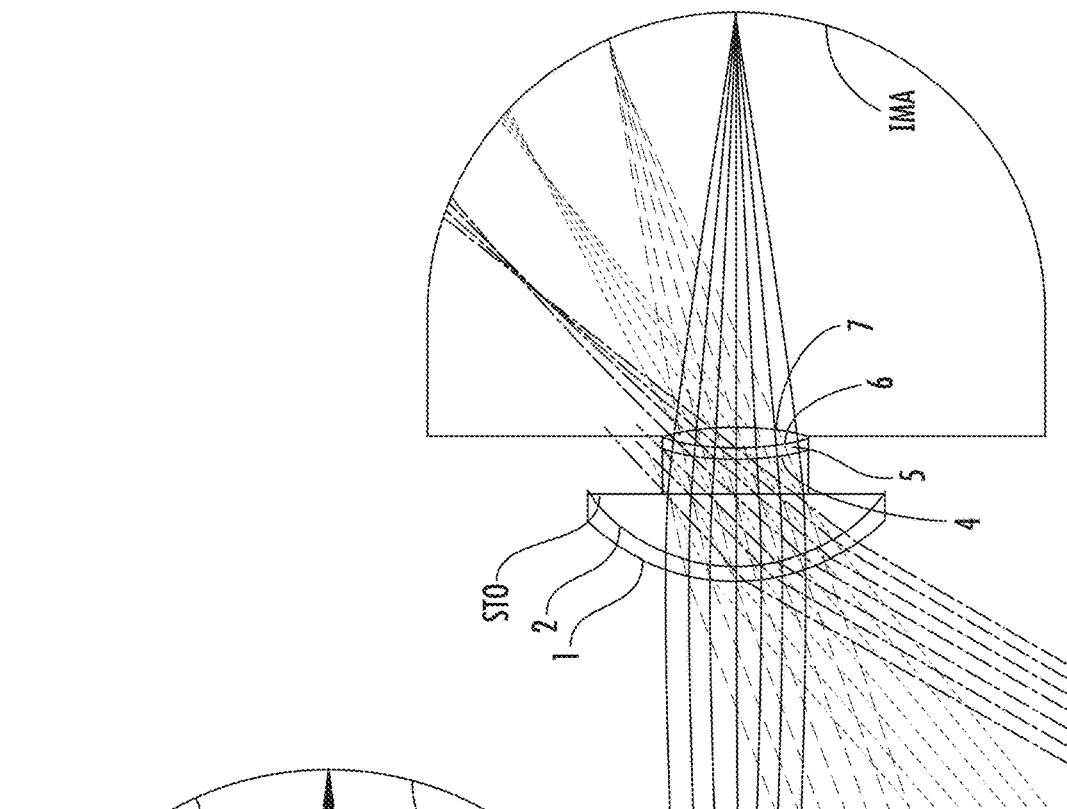
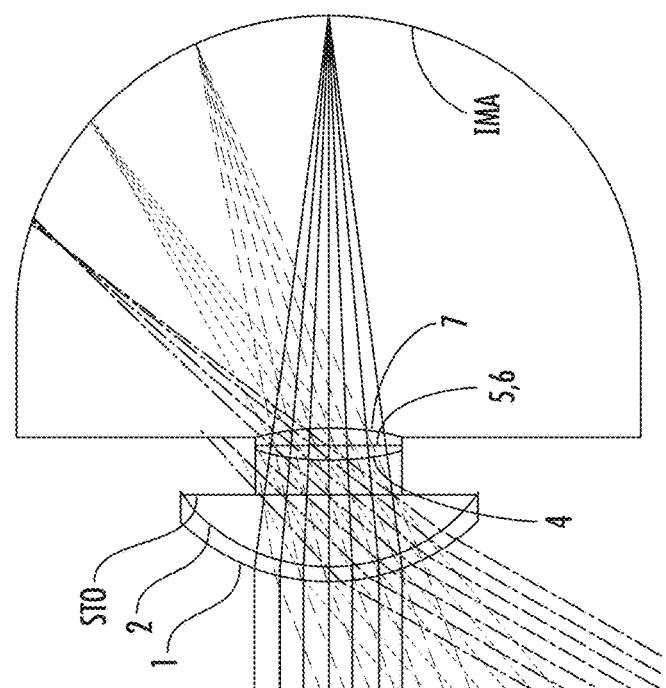
FIG. 7A
FIG. 7B

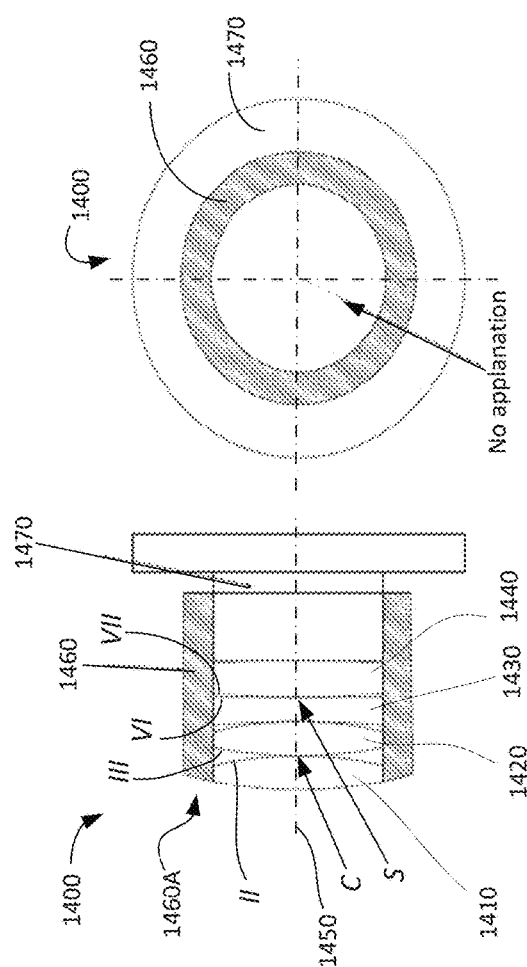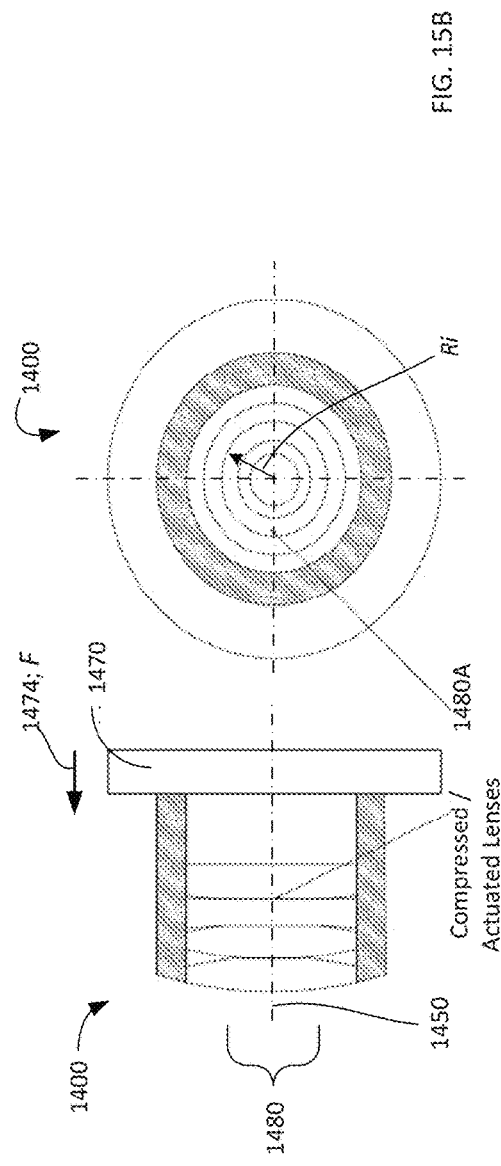

REFOCUSABLE LENS SYSTEM WITH MUTUALLY-APPLANATING INTERNAL SURFACES

CROSS-REFERENCE TO RELATED APPLICATIONS

The present application is a divisional of pending U.S. patent application Ser. No. 15/258,119 now published as US 2016/0374799, which in turn is a continuation of the International Patent Application No. PC/US2014/050318 filed on Aug. 8, 2014, which in turn designates the United States and claims priority from and benefit of the U.S. Provisional Patent Applications No. 61/949,268 filed on Mar. 7, 2014 and is a continuation-in-part of the U.S. patent application Ser. No. 14/334,514 filed on Jul. 17, 2014. The disclosure of each of the above-mentioned patent documents is incorporated herein by reference in its entirety.

TECHNICAL FIELD

The present invention relates to refocusable lens systems and, in particular, to lens systems having first and second aspherical surfaces that flatten each other in operation thereby continuously altering the effective focal length of the system. Such lens systems can be used in ophthalmological instruments (for example, as intraocular lenses) or opto-mechanical instruments employing a variable-focus lens.

BRIEF DESCRIPTION OF THE DRAWINGS

The invention will be more fully understood by referring to the following Detailed Description in conjunction with the generally not-to-scale Drawings, of which:

FIG. 1A is a diagram schematically showing, in side view, an embodiment of the anterior lens component of an embodiment of the invention;

FIG. 1B is a diagram schematically showing, in side view, an embodiment of the posterior lens component of an embodiment of the invention;

FIG. 2A is a diagram schematically illustrating a front view of an IOL according to one embodiment of the present invention, with haptics of the anterior and posterior lens components of FIGS. 1A, 1B interlocked;

FIG. 2B a diagram schematically illustrating the embodiment of FIG. 2A in side view;

FIGS. 5A, 5B schematically illustrate mutually-imposed deformation of a posterior surface of the anterior lens and an anterior surface of the posterior lens, of the embodiment of FIGS. 2A and 2B, causing a change of accommodating distance as a result of force transferred to the interlocked haptics of the IOL from ciliary muscle. FIG. 5A: accommodation at a near-distance point; FIG. 5B: accommodation at a far-away point;

FIGS. 7A, 7B illustrate layouts of a model of the human eye with the pseudophakic lens of the invention placed therein in Zemax® optical modeling software, showing the shape change of the front and back surface of the lens to alter the eye's focal distance from infinity to near;

FIGS. 14A and 14B are diagrams illustrating in side and front views an embodiment of a variable-focus lens system when no applanation is caused by mutually-facing internal surfaces of the system;

FIGS. 15A and 15B illustrate the side and front views of the embodiment of FIGS. 14, 14B after the array of individual lenses of the embodiment has been axially compressed;

SUMMARY

Figure 3:
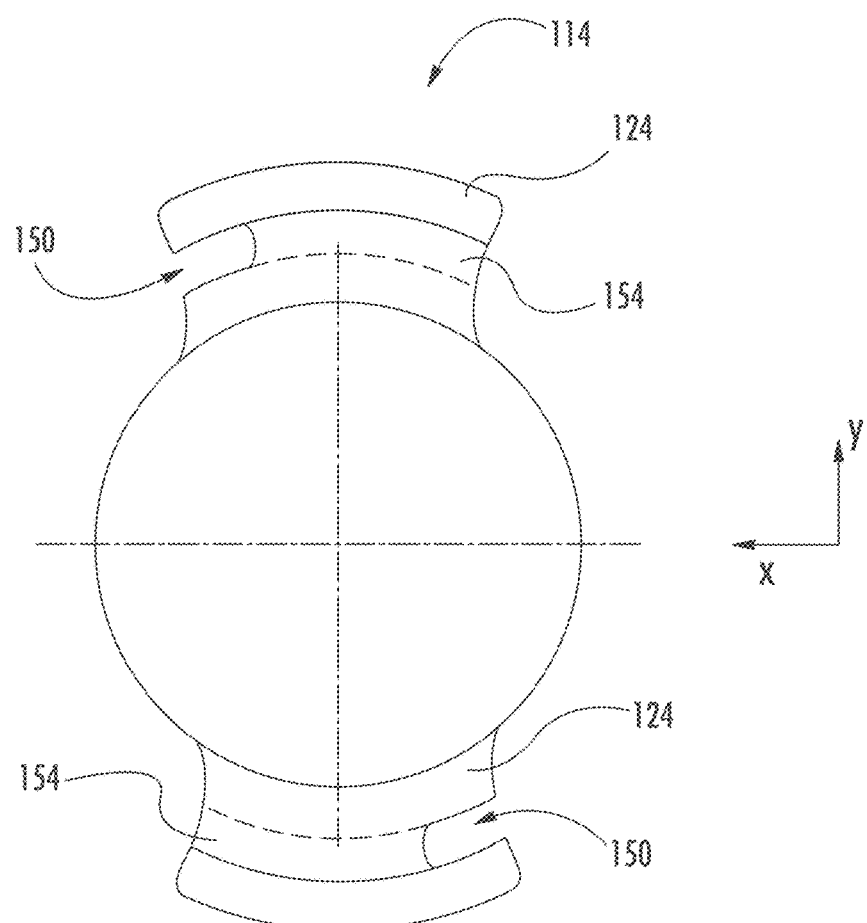
FIG. 3 schematically shows, in front view, a posterior lens component of FIG. 1B. Haptics of the posterior lens are shaped to include arced locking notches and interlocking grooves forming a portion of mechanism of interlocking between the anterior and posterior lens components. In a specific embodiment, an arced interlocking groove is substantially tangentially parallel to a perimeter of an optical portion of the associated lens.

Embodiments of the invention provide a pseudophakic lens assembly that contains a first lenslet having a first optical power and a first rotationally-symmetric optical portion defining a clear aperture of the first lenslet and a second lenslet having a second optical power and a second rotationally-symmetric optical portion defining a clear aperture of the second lenslet. The first lenslet includes at least two first haptic portions, each having a proximal end integrated with a peripheral region of the first optical portion and a distal free end. The second lenslet includes at least two second haptic portions respectively corresponding to the at least two first haptic portions, such that each of the at least two second haptic portions includes a notch and a groove. The groove is dimensioned to accommodate a corresponding distal free end therein when the first and second lenslets are coaxially positioned to define an axial point of contact between mutually-facing surfaces thereof such that each of the at least two first haptic portions is interlocked with the respectively corresponding of the at least two second haptic portions through the notch. The embodiment of the pseudophakic lens assembly is configured such as to increase an area of contact between the mutually-facing surfaces in response to a radially-vectored force transferred to the first and second rotationally-symmetric optical portions through the at least two first and second interlocked haptic portions.

In particular, die lens assembly can be configured such as to have an area of contact between the mutually-facing surfaces reduced in response to a radially-vectored force transferred to the first and second rotationally-symmetric optical portions through the at least two first and second interlocked haptic portions. Alternatively or in addition, the lens assembly is configured such as to have a portion of each of the mutually-facing surfaces applanated around an optical axis of the assembly in response to a radially-vectored force transferred to the first and second rotationally-symmetric optical portions through the at least two first and second interlocked haptic portions, thereby reducing the optical power of the assembly. In a specific embodiment, at least one of the mutually-facing surfaces in an unstressed state includes a prolate aspheric surface. In a related embodiment, a first haptic portion is interlocked with a second haptic portion as a result of a relative rotation of at least one of the first and second lenslets about an optical axis. An embodiment of the assembly may be configured to reduce at least one of the first and second optical powers in response to increasing a distance between free distal ends of the at least two first haptic portions that have been interlocked with the respectively corresponding of at least two second haptic portions.

In one specific embodiment, a pseudophakic lens assembly additionally includes a third lenslet having a third optical power and a third rotationally-symmetric optical portion defining a clear aperture of the third lenslet and at least two third haptic portions. The at least two third haptic portions are, in operation of the lens, interlocked with at least one of (i) the at least two first haptic portions and (ii) the at least two second haptic portions such as to define a point of contact between a first surface of the at least one of the first and second lenslets and a second surface of the third lenslet, wherein the first and second surfaces being are facing each other. The assembly is configured such that an area of contact between the first and second surfaces is changed in response to a radially-vectored force transferred to rotationally-symmetric portions of the assembly through interlocked haptic portions. Optionally, this specific embodiment is configured such as to have a portion of at least one of the first and second surface surfaces applanated around an optical axis of the assembly, in response to the radially-vectored force.

Embodiments of the invention further provide a method for operating a pseudophakic lens assembly. Such method includes juxtaposing first and second lenslets coaxially such that a surface of the first lenslet and a surface of the second lenslet face each other. These lenslets are configured such that the first lenslet includes at least two first haptic portions, each having a proximal end integrated with a peripheral region of the first optical portion and a distal end; and the second lenslet includes at least two second haptic portions respectively corresponding to the at least two first haptic portions. The method further includes interlocking each of these at least two first haptic portions with the respectively corresponding at least two second portions by rotating at least one of the first and second lenslets with respect to another about an axis such as (i) to form the lens assembly, in which the first and second lenslets are securely affixed to one another and (ii) to define an axial point of contact between said facing each other surfaces of the first and second lenslets. The method further includes varying an area of contact between the facing each other surfaces of the first and second lenslets in response to a radially-vectored force transferred to optical the first and second optical portions through the at least two first and second haptic portions interlocked with one another.

An embodiment of the method may additionally include applanating at least a portion of at least one of the facing each other surfaces of the first and second lenslets within the area of contact, and increasing the area of contact by increasing a distance between distal ends of the at least two first haptic portions. (In a specific embodiment, when only two lenslets are being juxtaposed, each lenslet may have a prolate aspheric surface in an unstressed state, and the step of varying includes causing prolate aspheric surfaces of the two lenslets to apply force towards one another such as to mutually applanate each other.) Alternatively or in addition, the method may contain a step of inserting the first and second lenslets individually into an eye through an incision in a cornea; and conforming a curvature of a posterior surface of the lens assembly to an internal surface of a natural lens capsule of the eye. In this specific case, the steps of juxtaposing and interlocking may be carried out after the step of inserting. In a related embodiment, the may additionally include changing an optical power of said pseudophakic lens assembly by causing the facing each other surfaces of the first and second lenslets to mutually deform each other. The step of changing an optical power may include changing a curvature of an axial portion of at least one of the facing each other surfaces of the first and second lenslets by a first amount while changing a curvature of an annular portion of said at least one of the facing each other surfaces by a second amount that is smaller than the first amount, where the annular portion circumscribes the axial portion. The step of interlocking may include affixing a first haptic portion in a notch of the second haptic portion and a corresponding distal end of the first haptic portion in a groove of the second haptic portion, said groove being substantially tangentially parallel to a perimeter of the first optical portion.

In a specific implementation, the method may additionally include the steps of (i) juxtaposing a third lenslet (having at least two third haptic portions) coaxially with said first and second lenslets, (ii) interlocking each of said at least two third haptic portions with at least one of respectively corresponding at least two first haptic portions, and respectively corresponding at least two second haptic portions. The interlocking is achieved by rotating at least one of said first, second, and third lenslets about an axis such as (a) to form a second lens assembly, in which the first, second, and third lenslets are securely affixed to one another and (b) to define a point of contact between first and second facing each other immediately adjacent surfaces, the first surface being a surface of the third lenslet and a second surface being a surface of at least one of the first and second lenslets. The specific implementation of the method may be complemented by a step of varying a second area of contact between said first and second surfaces in response to the radially-vectored force, which varying may optionally include causing at least one of the first and second surfaces to apply force towards one another such as to applanate at least one of the first and second surfaces.

Embodiments additionally provide a variable-focal-length lens system that includes (i) a first lenslet having a first optical power and a first rotationally-symmetric optical portion defining a clear aperture of the first lenslet, and (ii) a second lenslet having a second optical power and a second rotationally-symmetric optical portion defining a clear aperture of the second lenslet, such that the first and second lenslets are disposed co-axially to define a contact between surfaces thereof at an axial point. The system additionally includes means for transfer of motion applied to a surface of at least one of the first and second lenslets to a force applanating at least one of said surfaces about the axial point such that an area of applanation of the surface in question depends on a degree of such motion. The system may be equipped with a housing unit enclosing the first and second lenslets and mechanically cooperated with the means of transfer of motion which, in a specific case, may include a piston movable internally with respect to the housing. In one embodiment, the lens system is configured to have a first surface of the first lenslet and a second surface of the second lenslet interact with one another, in response to a non-zero force transferred to at least one of the first and second surfaces by said means, such as to mutually applanate one another to define respective applanated areas diameters of which progressively increase with increase in such non-zero force created by means for transfer of motion. In a specific case, a process of increase in a diameter of an applanated area of any of the first and second surfaces response to increase of such force, optical aberrations of the lens system that are caused by changes in the diameter of the applanated area are minimized.

DETAILED DESCRIPTION

Needs for a variable-focus lens system are numerous and range from uses in optical engineering (such as, for example, in a photocamera) to uses in medicine (for example, as an ophthalmological element). While the idea of the present invention was facilitated by the ophthalmological use of a variable-focus lens, the following disclosure additionally presents related embodiments the application of which goes beyond ophthalmology.

To this end, references throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, it is to be understood that no single drawing is intended or even capable to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

The invention as recited in claims appended to this disclosure is intended to be assessed in light of the disclosure as a whole.

One common need of a variable-focus lens arises as a result of the clouding of die natural lens of an eye, which is often age-related, referred to as cataract. Visual loss, caused by the cataract, occurs because opacification of the lens obstructs light from traversing the lens and being properly focused on to the retina. The cataract causes progressive decreased vision along with a progressive decrease in the individual's ability to function in his daily activities. This decrease in function with time can become quite severe, and may lead to blindness. The cataract is the most common cause of blindness worldwide and is conventionally treated with cataract surgery, which has been the most common type of surgery in the United States for more than 30 years and the frequency of use of which is increasing. As a result of cataract surgery, the opacified, clouded natural crystalline lens of an eye is removed and replaced with a synthetic and clear, optically transparent substitute lens (often referred to as an intraocular lens or IOL) to restore the vision.

The use of such customized synthetic IOLs that are properly sized for a given individual—often referred to as intraocular lenses—has been proven very successful at restoring vision for a predetermined, fixed focal distance. The most common type of IOL for cataract treatment is known as pseudophakic IOL that is used to replace the clouded over crystalline lens. (Another type of IOL, more commonly known as a phakic intraocular lens (PIOL), is a lens which is placed over the existing natural lens used in refractive surgery to change the eye's optical power as a treatment for myopia or nearsightedness.) An IOL usually includes of a small plastic lens with plastic side struts (referred to as "haptics"), which hold the IOL in place within the capsular bag inside the eye. IOLs were traditionally made of an inflexible material (such as PMMA, for example), although this is being superseded by the use of flexible materials. Such lenses, however, are not adapted to restore the eye's ability to accommodate, as most IOLs fitted to an individual patient today are monofocal lenses (lenses with a fixed, single position of a focal point) that are matched to "distance vision".

Accommodation is the eye's natural ability to change the shape of its lens and thereby change the lens' focal distance. The accommodation of the eye allows an individual to focus on an object at any given distance within the field-of-view (FOV) with a feedback response of an autonomic nervous system. Accommodation of an eye occurs unconsciously, without thinking, by innervating a ciliary body muscle in the eye. The ciliary muscle adjusts radial tension on the natural lens and changes the lens' curvature which, in turn, adjusts the focal distance of the eye's lens.

Without the ability to accommodate one's eye, a person has to rely on auxiliary, external lenses (such as those used in reading glasses, for example) to focus his vision on desired objects. Typically, cataract surgery will leave an individual with a substantially fixed focal distance, usually greater than 20 feet. This allows the individual to participate in critical activities, such as driving, without using glasses. For activities such as computer work or reading (which require accommodation of eye(s) at much shorter distance), the individual then needs a separate pair of glasses.

Several attempts have been made to restore eye accommodation as corollary to cataract surgery. Some of contemporary IOL designs attempt to exploit the optical effect of anterior lens displacement that produces myopic shift and thus improve near vision; early clinical evaluation confirmed some degree of accommodative effect that is proportional to the measured displacement of the optic.

The most successful of used methodologies relies on using a substitute lens that has two or three discrete focal lengths to provide a patient with limited visual accommodation in that optimized viewing is provided at discrete distance—optionally, both for distance vision and near vision. Such IOLs are sometimes referred to as a "multifocal IOLs". The practical result of using such IOLs has been fair, but the design compromises the overall quality of vision. Indeed, such multifocal IOLs use a biconvex lens combined with a Fresnel prism to create two or more discreet focal distances. The focal distance to be utilized is in focus while there is a superimposed defocused image from the other focal distances inherent in the lens. Also, the Fresnel prism contains a series of imperfect dielectric boundary-related discontinuities, which create scatter perceived as glare by the patient. Some patients report glare and halos at night time with these lenses.

Another methodology may employ altering die position of a fixed-focal-length substitute lens (often referred to as an "accommodating IOL") with contraction of a ciliary muscle to achieve a change in the working distance of the eye. These "accommodating IOLs" interact with ciliary muscles and zonules, using hinges at both ends to "latch on" and move forward and backward inside the eye using the same natural accommodation mechanism. In other words, while the fixed focal length of such IOL does not change in operation, the focal point of an "accommodating IOL" is repositioned (due to a back-and-forth movement of the IOL itself) thereby changing the working distance between the retina and the IOL and, effectively, changing the working distance of the IOL. Such IOL typically has an approximately 4.5-mm square-edged optical portion and a long hinged plate design with polyimide loops at the end of the haptics. The hinges are made of an advanced silicone (such as BioSil). While "accommodating IOLs" have the potential to eliminate or reduce the dependence on glasses after cataract surgery and, for some, may be a better alternative to refractive lens exchange (RLE) and monovision, this design has diminished in popularity due to poor performance and dynamic range of movement that is not sufficient for proper physiological performance of the eye.

Another shortcoming of the use of most currently existing structures of accommodating lenses is known to be inability to perform a laser capsulotomy procedure (to remove a film growth over the ventral posterior surface of the lens capsule, which degrades the vision, as a result of which the spatial continuity of the capsule across the whole posterior surface of the IOL lens may become uncertain.

Therefore, there remains an unresolved need in an IOL that is structured to be, in operation, continuously accommodating, with gradually, non-discretely and/or monotonically adjustable focal length.

According to an embodiment of the invention, the problem of accommodating the focal length of an IOL is solved by forming the IOL as a coaxial assembly of at least two individual interlocked-through-the-haptics lenslets and utilizing a force mechanism supplied by the eye's ciliary muscle to vary an area of contact of facing each other surfaces of such lenslets and to applanate these surfaces within the area of contact. The individual lenslets of the IOL assembly are provided with at least one flexible prolate aspherical surface the curvature of which is juxtaposed in such spatial relation with respect to the ciliary muscle that force, transferred to the optical portion of the IOL through the interlocked haptics by the muscle, applies pressure on the facing each other surfaces of the immediately adjacent individual lenslets to change the curvatures of such surfaces in the area of contact and, thereby, the optical power of the overall IOL as well. Such variation of the focal length is achieved without substantial repositioning of the IOL itself.

According to a related embodiment of the invention, the problem of varying the focal length of a multi-lens optical system is solved by providing a co-axially queued individual lenses, at least two of which are in contact at a point located at the axis, and utilizing a means for axially compressing at least a portion of this array of lenses such that lens surfaces that are in contact at the axial point deform each other in response to the axially-applied pressure and, optionally, in response to minute axial movement of a component of the system) to increase an area, of each surface, that is applanated. The applanation of the mutually-deforming internal surfaces of the lens system is reversible in response to reverse operation of means for axial compression that causes the reduction of force with which one of the contacting-each-other surfaces interacts with another.

Numbering of structural surfaces. In describing the order of elements or components in an embodiment of a lens system of the invention or a sub-set of such system, the following convention will be generally followed herein, unless stated otherwise. The order in which the surfaces of sequentially positioned structural elements of the lens assembly are viewed along a direction of light incident on the lens system, in operation and/or when installed, from the object is the ascending order in which these surfaces are referred to as the first surface (or surface I), the second surface (or surface II), the third surface (or surface III), the fourth surface (or surface IV) and other surfaces if present. For example, in the case of an embodiment shown in FIGS. 1A, 1B, the direction of incidence of light is indicated as the z-axis. Generally, therefore, surfaces of the structural elements (such as substrates) of an embodiment of the invention are numerically labeled starting with a surface that corresponds to the front portion of the lens system and that is proximal to the object and ending with a surface that corresponds to the back portion of an assembly and that is proximal to the retina. Accordingly, the term "behind" refers to a position, in space, following a position of something else and suggests that one element or thing is at the back of another as viewed from the front of the lens assembly. Similarly, the term "in front of" refers to a forward place or position, with respect to a particular element as viewed from the front of the assembly.

Examples of Embodiments for Ophthalmic Use.

FIGS. 1A and 1B schematically illustrate, in side view, an anterior lens 110 and a posterior lens 114, each equipped with corresponding flexible haptic elements 120, 124 structured to interlock the individual lens components (or lenses, lenticles, lenslets) 110, 114 together to form, in operation, an interlocked embodiment of the intraocular lens system. An example of such embodiment is shown as 200 in FIGS. 2A and 2B. The side structures, or haptics. 120, 124 hold the lens system in place within the capsular bag inside the eye (as later discussed in reference to FIG. 4). (It is appreciated that, generally, more than two—for example three, four, or more—lenslets in series may be used to for ti an embodiment of the invention. In an embodiment in which more than two intercoupled lenslets components are used to for u an IOL, the operation of the IOL includes a deformation of multiple surfaces that are internal to the IOL. For simplicity of illustration, the structure of the IOL that includes more than two lenses in series is not shown, as the principle of its operation is substantially similar to that described below in reference to the IOL including two lenslets.) In a specific implementation, the optical portions 126, 128 of lenses 110, 114 (shown, in this embodiment, with beveled peripheral edges 126A, 128A) have mutually-opposing surfaces 132, 136, (or surfaces II and III) each having, in a specific case, a corresponding prolate aspherical shape (although these opposing surfaces can generally be shaped differently).

Each of the lenses 110, 114 are deformable and foldable, and are made from silicone and/or acrylic materials commonly used for construction of IOLs such as, for example, foldable/flexible hydrophobic and/or hydrophilic acrylic, silicone, hydrogel, collamer, and/or rigid PMMA when required.

The interlocking haptic element 120 and the stabilizing haptic element 124 are shown to include two portions each (the upper portion and the lower portion, as seen in FIGS. 1A, 1B), the corresponding portions of the anterior lens haptic 120 and the posterior lens haptic 124 being paired in operation. However, a chosen lens may have different number of haptic portions—for example, three, or more—and other lens(es) of the system will have, in this case, respectively corresponding haptic portions for pairing with the ones of the chosen lens. In one implementation the haptics are symmetric about an optical axis 130. Haptics of lenses 120, 124 define monotonically-curved, for example oval, outer surfaces (as shown, surfaces 140, 144) in absence of mechanical stress. As shown in FIG. 3, at least one of the haptic portions 124 of the posterior lens 114 includes a locking notch 1:50 in the wing-portion of the haptic and an interlocking haptic channel or groove 154 dimensioned, in the posterior surface of the lens 114, to fixatedly and securely accommodate the interlocking haptic extensions 120 of the anterior lens 110 when the two lenses 110, 114 are being interlocked. While the interlocking haptic-accommodating groove 154 is shown to extend, in the surface 144, along an arc to an edge of the haptic element 124, in an alternative implementation the groove or channel 154 may be terminated earlier, before the edge of the haptic 124.

In practice, the lenses 110, 114 are inserted individually, separately, while folded, through a small incision in the eye (typically, under 3 or even 2 mm in size) to minimize surgical trauma, unfolded in the volume defined by the capsular sack such as to ensure that the curved surfaces 140, 144 and the outer surfaces I, II conform to the shape of the lens capsule. The lenses are then coupled together by rotating of one of the lenses with respect to another about the optical axis (axis z as shown in FIGS. 1A, 1B) to pass an interlocking haptic 120 through a notch 150 such that the end of the haptic 120 is rested in and along the interlocking channel 154 of the stabilizing haptic 154. As a result of such interlocking, a portion of a haptic 120 that is proximal to the optical portion of the lens 110 is located in front of a stabilizing haptic 124 of the lens 114 and in the notch 150, while a portion of a haptic 120 that is distal to the optical portion of the lens 110 is located behind the haptic 124 of the lens 114, in the groove 154. The haptics are structured such that, in the interlocked position, the surfaces II, III (the inner surfaces of the IOL system) are placed in contact at the axial point P (in a specific embodiment—without substantial deformation of surfaces II, III) to provide full refractive power of the surfaces II, III for near-distance accommodation of the IOL system, while the interlocked haptics exert small redial pressure on the natural lens capsule along the IOL-system's long axis.

The haptics 120, 124 are designed to be supported in their rigidity within the natural lens capsule retained following the cataract extraction (shaped as a lobsided oval in a cross-section, with the long axis of about 8.2 mm and a short axis of about 4.2 mm, with the anterior curvature of approximately 9 mm and posterior curvature of about 6.5 mm). The outer limits of the haptics are flared with rounded edges to distribute stress over a large area of the capsule, which limits non-azimuthally symmetric deformation and the risk of capsular rupture. The haptics are structured to conform to the posterior surface of the capsule out to its equator and, when so conformed, are able to counter the net anterior vector of force by transmitting the force centripetally to the equator of the capsule. Lastly, the haptics are designed to have such a width as to increase their rigidity and prevent rotational buckling.

It is noted that one operational shortcoming of some of existing to-date mechanical structures of accommodating IOLs of the related art is that the small force applied by the capsule 116 to the lens is not sufficient to actuate the lens and alter its shape and power. In contradistinction with accommodating IOLs of the related art, embodiments of the present invention are structured to directly transfer the force, caused by flexing of the ciliary body muscle, to the mutually opposing surfaces II, III of the optical portions of the component lenses 110, 114 such as to alter their shapes, causing substantially no loss of force upon transmission that would otherwise occur if the force were transferred to any other an internal or anterior surface of the optical portion of the embodiment (For example, in one embodiment, the small actuating/accommodating force of about 1 gram is sufficient for the operation of the lens of the present invention.)

Figure 4:
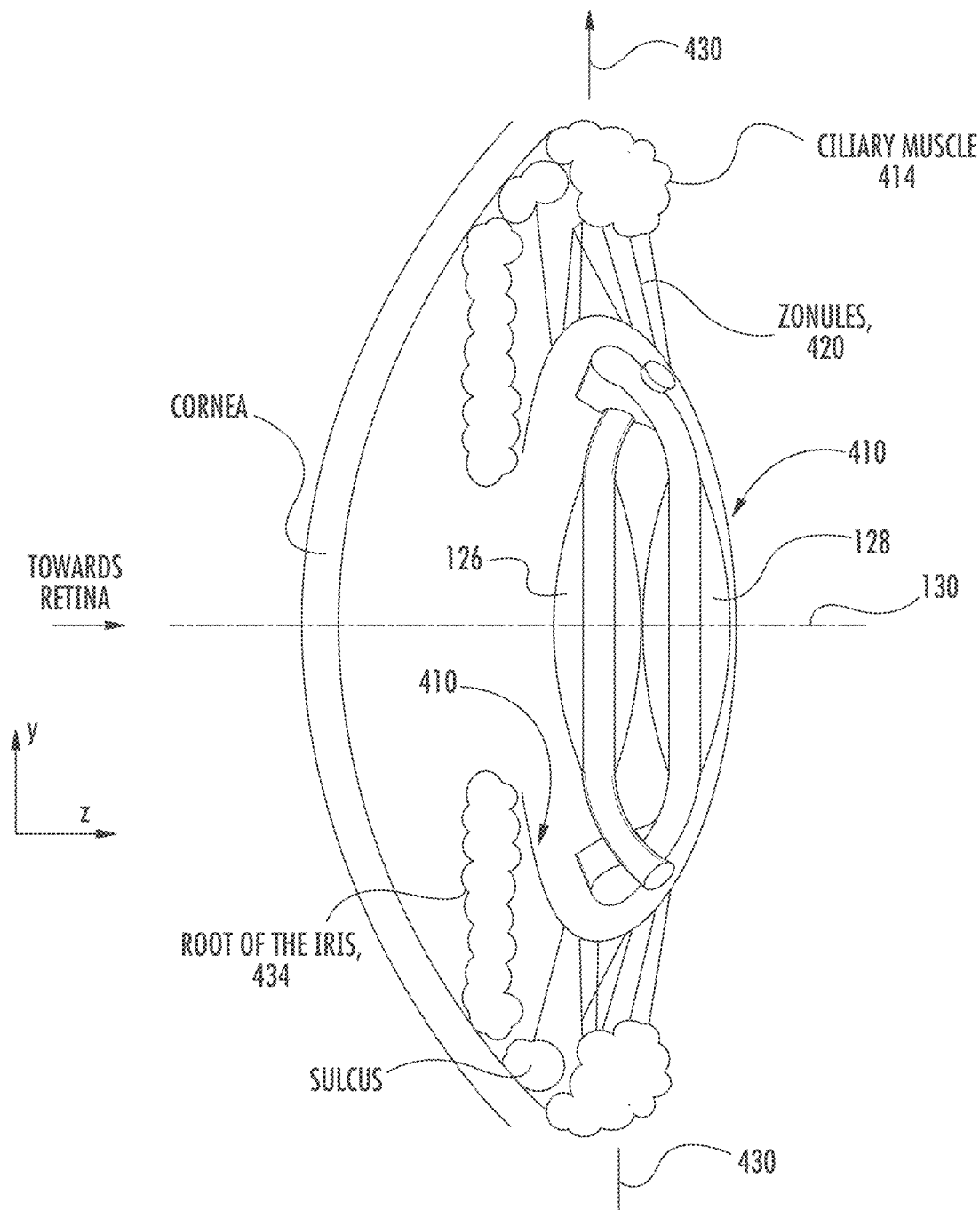
FIG. 4 is a diagram illustrating an example of operable placement of the embodiment of FIGS. 2A, 2B in a capsule membrane of an eye in place of a natural eye lens.
Figure 10:
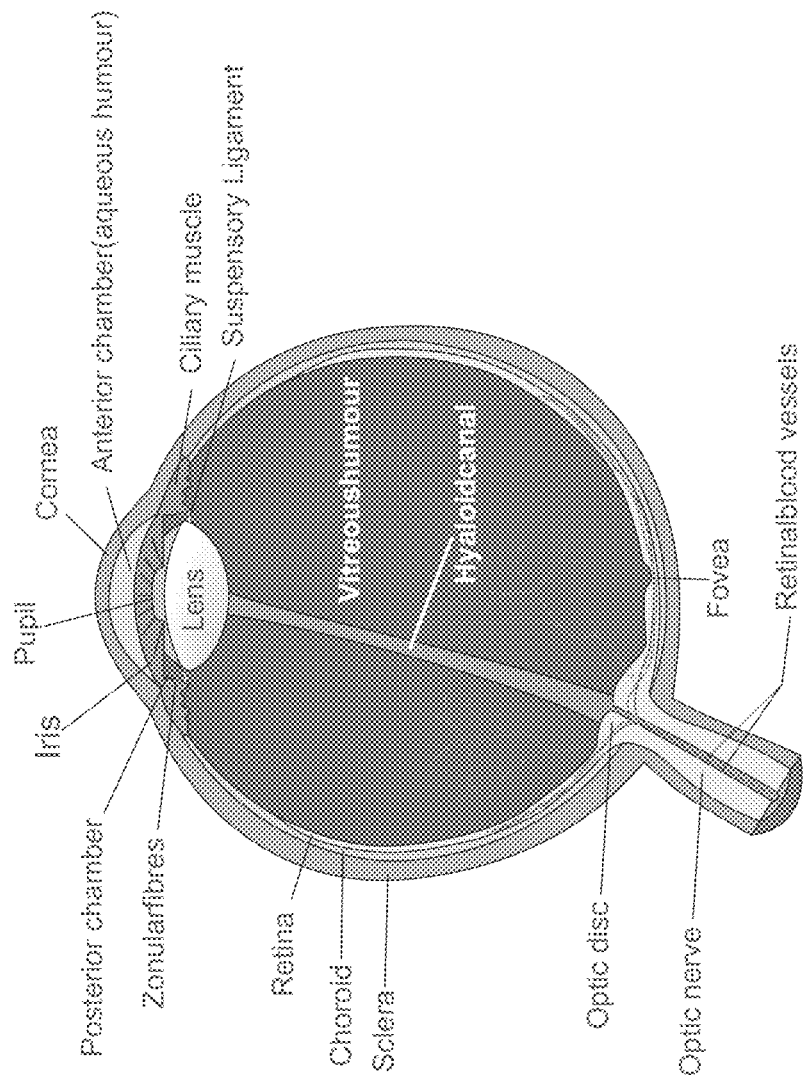
FIG. 10 is a diagram of a human eye.

FIG. 10 shows diagrammatically the human eye. To this end, and in reference to FIG. 10, FIG. 4 illustrates, in a simplified cross-sectional view, an example of operable cooperation with and spatial orientation of the embodiment 200 inside the eye. Each of the individual lenses 126, 128 can be inserted individually, while folded due to the flexibility of the material they are made from, through an approximately 3 mm incision in the eye (which is a currently used approach), to reduce trauma to the eye. Following the insertion, the lenses 126, 128 are interlocked to form the IOL 200.

Upon the formation of the interlocked IOL system, the free ends of the interlocked haptics 120, 124—which are distal to optical portions of the corresponding lenses—are placed in the lens capsule (also referred to as capsule bag) 410 of the now-removed natural lens of the eye to be abutted against the equatorial portion of the capsule 410 (against the capsule in the peripheral portion of the volume defined by it). The lens capsule does not adhere to silicone, and therefore the optics is kept in place by the haptics. When the ciliary body muscle 414 is relaxing (for example, during the focusing of the eye at a large distance), tension on the zonules (ciliary zonules) 420 and/or the capsule 410 is increased centripetally. As a result, a force 430, vectored outwardly from the axis 130 and created by tension of zonules 420, increases the radial diameter of the IOL system-retaining lens capsule 410, thereby reducing the pressure exerted by the interlocked haptics 120, 124 onto the capsule 410 and allowing the previously radially-compressed interlocked haptics 120, 124 expand radially, which is accompanied by an axial compression of the lens' optics and decreasing the overall axial thickness I) of the system to d<D, as a schematic diagram of FIGS. 5A, 5B illustrate.

The axial compression of the IOL system is additionally bolstered by the compression of the overlying posterior capsule 410, in which the posterior stabilizing haptics 124 are preventing anterior displacement of the coupled lenses 110, 114. It is worth noting, that in order for such "facilitating" compression of the capsule to occur, the capsule does not have to be necessarily spatially continuous across the whole posterior surface of the IOL system (which, in case of the embodiment 200 is surface IV). As a result, the lens-system of the present invention is operable to achieve the goal of focal accommodation even in the case when a very common post-cataract surgery procedure (commonly referred to as an Nd-YAG laser capsulotomy, which removes a film growth that degrades vision over the central posterior surface of the lens capsule) has been performed.

Figure 6:
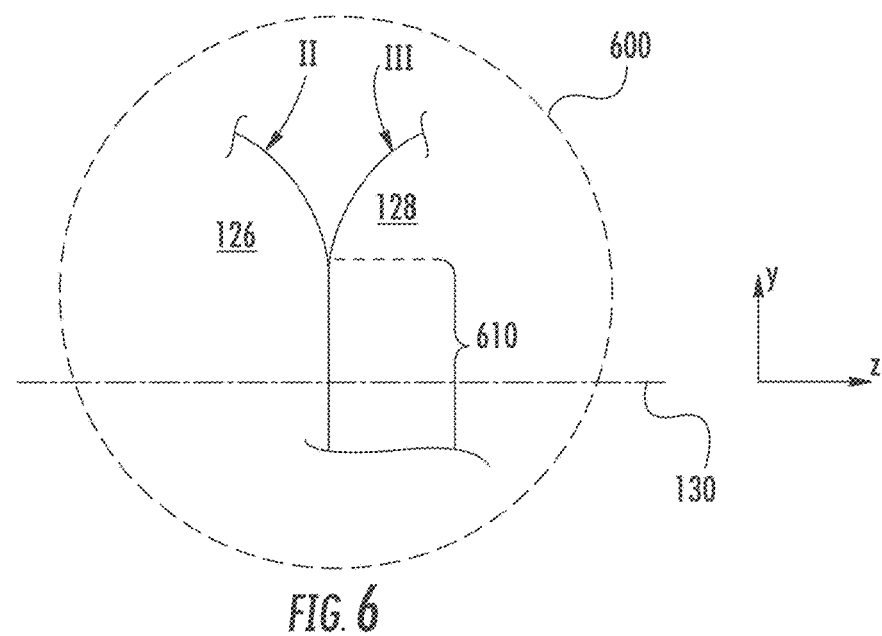
FIG. 6 schematically shows an enlarged central portion of the embodiment of FIG. 5B, illustrating the mutually-imposed flattening of the contacting surfaces of the embodiment that accompanies the accommodation of the IOL at a long distance.

Referring again to FIGS. 5A, 5B and in further reference to FIG. 6, showing the enlarged central, axial portion 600 of the lens of FIG. 5B and specifically surfaces II and III in contact, it is understood that as a result of the combination of the equatorial elongation and the axial compression of the interlocked lenses 126, 128, surfaces II and III mutually deforming (deforming each other) such as to define a flattened area 610 across which these surfaces are in continuous contact and are flattened (due to the pliability of the material of the individual lenses 126, 128) as compared to the shape of these surfaces shown in FIGS. 2B and 5A, when the ciliary muscle is not relaxed. In one embodiment, such flattened (applanated) area 610 is axially symmetric about the axis 130. The flattening of surfaces II and III due to the mutual deformation of the lenses 126, 128 effectively reduces optical contributions of each of these surfaces to the power of the overall lens 114 substantially without any direct contribution from axial translation (of an optical component of the overall lens) to the accommodation of the IOL 200.

Stated differently, during the contraction of the ciliary muscle, the pulling force applied to the embodiment of the installed IOL radially (or outwardly with respect to the axis of the lens) extends the haptics outwardly, which mechanically translates into an axial force that pushes individual lenses of the IOL axially towards each other thereby increasing the region of contact between the facing-each-surface of the IOL from the axial point to some measurable area surrounding the axial point. As a result, in such region of contact the facing-each-other surfaces of lenses are applanated, and the overall power of the system is reduced, resulting in accommodation at large distance (for example, infinity). During the relaxation of the ciliary muscle, on the other hand, the axial force is reduced and the region of contact between the individual lenses is reduced, thereby increasing the curvatures of the lens' surfaces within the region of contact and increasing the overall power of the system, thereby accommodating the IOL accommodation at a near distance. In a specific embodiment, the radii of curvature of the facing-each-other surfaces II and III are larger than those of the outer surfaces I and IV.

FIGS. 7A, 7B provide diagrams schematically illustrating an optical layout used for ray-tracing of light through a model of an eye (in which the natural lens is substituted with an embodiment of the IOL according to the invention) from the object towards the retina to illustrate the ability of the embodiment of the invention to refocus within a dynamic range of distances (from infinity, corresponding to the layout of FIG. 7A, to a near-distance which, in the case illustrate in FIG. 7B is about 100 mm), which dynamic range substantially exceeds requirements that can be encountered in practice. Examples of Zemax® model design parameters corresponding to the layouts of FIGS. 7A, 7B are presented in Tables 1 and 2, respectively. The pupil stop was set for 5.1 mm (for accommodation at infinity) and 3 mm for near-distance accommodation. Surfaces 1, 2 represent the surfaces of die cornea; surface 3 (labelled as "STO") corresponds to the aperture stop; surfaces 4, 5 correspond to surfaces I and II of the anterior lens 126, while surfaces 6, 7 correspond to surfaces III and IV of the posterior lens 128, respectively. Surface "IMA" corresponds to a surface of the retina.

Figure 8A:
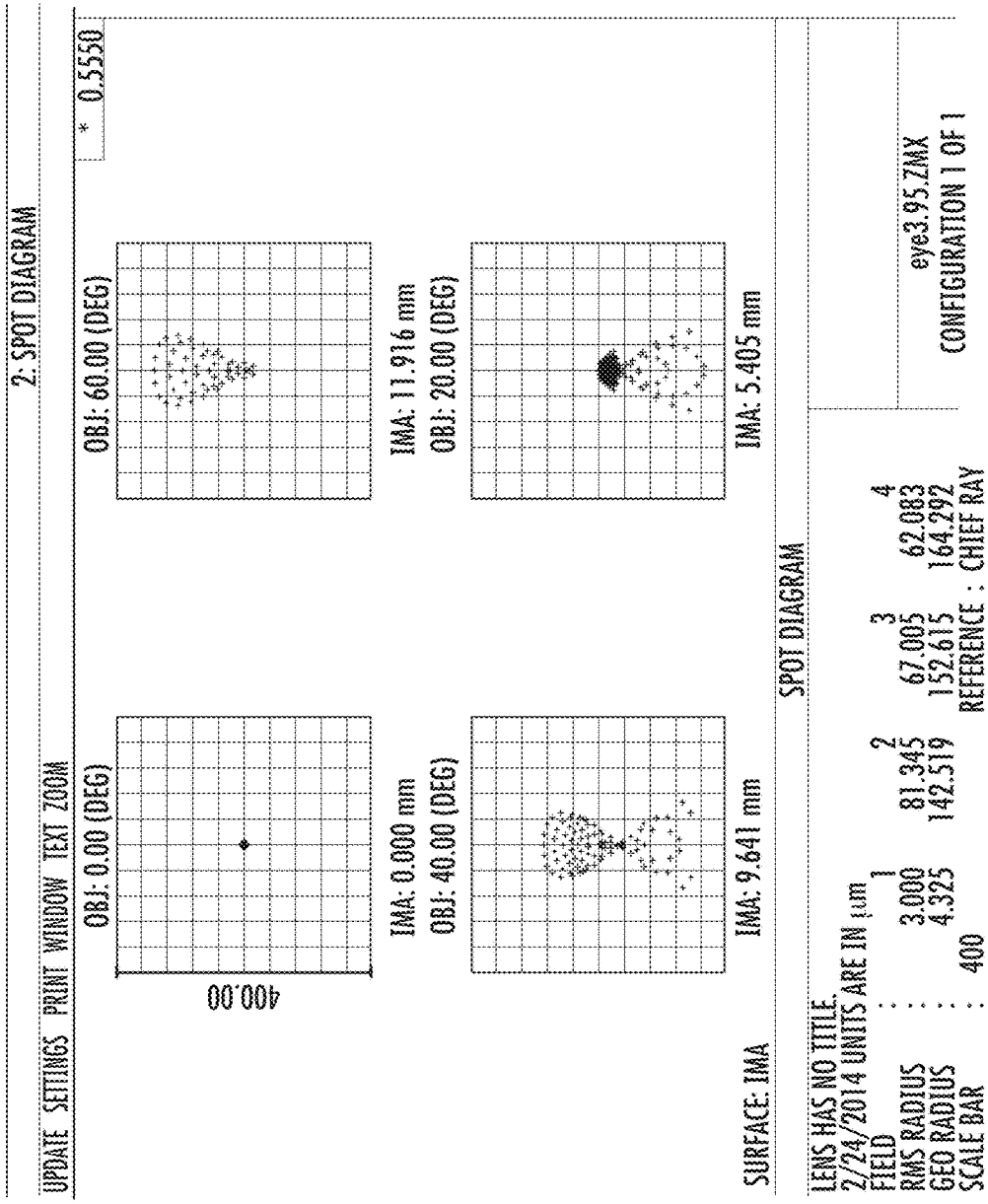
FIGS. 8A, 8B present spot diagrams generated in Zemax® and corresponding, respectively, to layouts of FIGS. 7A, 7B.
Figure 8B:
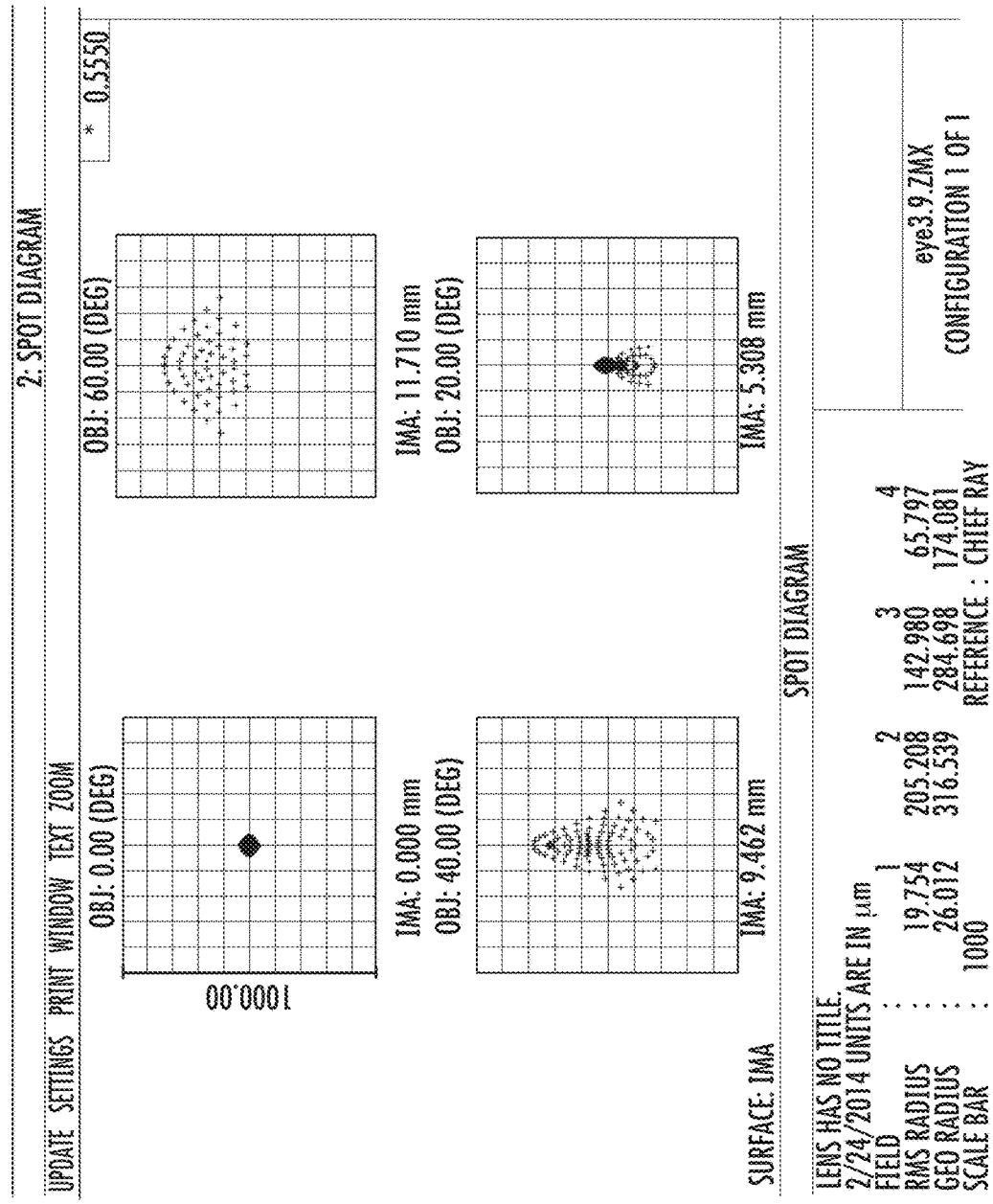
Figure 9A:
FIGS. 9A, 9B show images of the same object formed with an embodiment of the invention accommodated according to the layouts of FIGS. 7A, 7B.
Figure 9B:

It is appreciated that the particular example of the IOL design for near/short distance accommodation was set to a 100 mm distance to object (FIG. 59) to more clearly illustrate a change of curvatures of the mutually-deforming upon variable contact surfaces 5, 6 (II, III) with the change of accommodation of the IOL from the infinity to a near point object. It can be seen that, while for accommodation at infinity (FIG. 7A) the surfaces 5, 6 are flattened and in contact across a substantial portion of clear apertures of the lenses 126, 128, for a near-distance accommodation the contact area between the surfaces 5, 6 is substantially reduced to a small region about the optical axis. In practice, as would be appreciated by a skilled artisan, the actual physiological design of the IOL 200 would be optimized for a near distance to object of about 200 mm or so. All design parameters summarized in Tables 1, 2 are initial estimates and not necessarily optimized and, therefore, corresponding spot diagrams (of FIGS. 8A, 8B) and simulated images (of FIGS. 9A, 9B) do not necessarily reflect the best quality of imaging achievable with an embodiment of the IOL of the invention,

TABLE 1

Zemax ® design parameters corresponding to layout of FIG. 7A

| Surf: Type | | Radius | Thickness | Glass | Semi-Diameter | | Conic |
|---|---|---|---|---|---|---|---|
| OBJ | Standard | Infinity | 1.000E+004 | | 1.733E+004 | | 0.000 |
| 1* | Standard | 7.800 | 0.550 | 377571 | 6.000 | U | −0.600 |
| 2* | Standard | 7.800 | 2.970 | 337613 | 6.000 | U | −0.100 |
| STO* | Standard | Infinity | 1.500 | 337613 | 2.800 | U | 0.000 |
| 4* | Standard | 11.100 | 0.700 | 470519 | 3.000 | U | 0.000 |
| 5* | Standard | Infinity | 0.000 | 337613 | 3.000 | U | −2.000 |
| 6* | Standard | Infinity | 0.700 | 470519 | 3.000 | U | −2.000 |
| 7* | Standard | −11.100 | 16.930 | 336611 | 3.000 | U | −2.000 |
| IMA | Standard | −13.400 | — | 336611 | 12.600 | U | 0.150 |

TABLE 2

Zemax ® design parameters corresponding to layout of FIG. 7B

| Surf: Type | | Radius | Thickness | Glass | Semi-Diameter | | Conic |
|---|---|---|---|---|---|---|---|
| OBJ | Standard | Infinity | 100.000 | | 178.337 | | 0.000 |
| 1* | Standard | 7.800 | 0.550 | 377571 | 6.000 | U | −0.600 |
| 2* | Standard | 7.000 | 2.970 | 337613 | 6.000 | U | −0.100 |
| STO* | Standard | Infinity | 1.500 | 337613 | 2.800 | U | 0.000 |
| 4* | Standard | 11.100 | 0.700 | 470519 | 3.000 | U | 0.000 |
| 5* | Standard | −22.000 | 0.000 | 337613 | 3.000 | U | −2.000 |
| 6* | Standard | 22.000 | 0.700 | 470519 | 3.000 | U | −2.000 |
| 7* | Standard | −11.100 | 16.930 | 336611 | 3.000 | U | −2.000 |
| IMA | Standard | −13.400 | — | 336611 | 12.600 | U | 0.150 |

Figure 12:
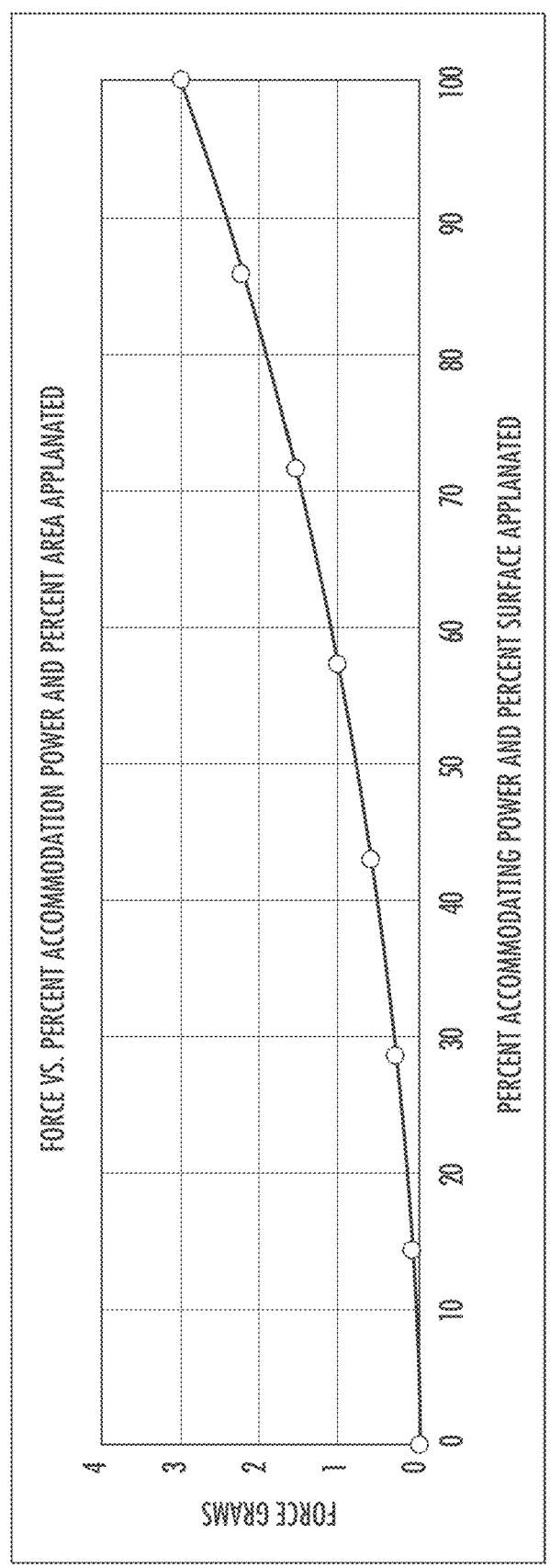
FIG. 12 is a plot showing a dependence of a degree of surface applanation of an embodiment of FIGS. 7A, 7B as a function of force transferred to the surface.

The degree of mutually-caused applanation (of the facing each other surfaces II, III of the embodiment of FIGS. 5A, 5B the parameters of which are listed in Tables 1 and 2) as a function of force applied to the lens surfaces is shown in FIG. 12, showing a substantially quadratic response of a lens' surface.

In a specific embodiment in which surfaces II and III possess prolate asphericity in die unstressed state (as schematically illustrated in FIGS. 1A, 1B, 2B, 5A), parameters of such asphericity are judiciously chosen to increase the efficiency of operation of the IOL 200 by taking advantage of natural miosis, as compared to the case when surfaces II and III are spherical, for example. Miosis (pupillary constriction) accompanies eye-lens accommodation to a near object. Due to the very shape of the prolate aspheric, the central portion of the IOL 200 located very close to the optical axis 130 has increased optical power as compared to the outer, peripheral portion of the IOL. When the pupil of the eye is constricted during near-distance accommodation, the clear aperture of the eye corresponds to only the small central portion of the unstressed lens, where the maximum curvature occurs in the prolate asphere, while the contribution of the peripheral portion of the lens having lower power contribution than that of the utilized central portion is not utilized. Conversely, during the long-distance accommodation of the eye with the IOL 200, the clear aperture of the eye is larger (due to papillary dilation accompanying such long-distance accommodation), while the mutual flattening of surfaces II and iiI in the area 610 of the IOL 200 (which includes both the central, axial portion of the lens and at least some of the peripheral portion of the lens that) reduces the contribution of the area 610 to the overall power of the lens. Accordingly, the amount of force that the ciliary muscle has to apply to achieve a certain degree of accommodation of a embodiment of the lens two facing each other surfaces of which are prolate aspheric is advantageously smaller that that required to achieve the same degree of accommodation when the surfaces at hand are either spherical or, generally, have a shape differing from prolate aspheric. FIG. 9 illustrates a dependence of accommodation power and a degree of applanation in an embodiment of IOL 114 as a function of the equatorial force applied to the haptics of the IOL 200 having optical, geometrical, and material parameters discussed above The data presented in FIG. 9 were calculated the formula is based the closest fit curve to a finite element analysis model, which follows the general form of "Applanating Force—A* (Applanated Area)$^2$"; here, the factor A incorporates both the modulus of elasticity of the material of the lens and the curvature of the opposing surface. The percent applanated area is substantially linearly related to the percent lens power. The assumptions used in such assessment include: negation of the lens power contributed by the inner opposing surfaces of the IOL over the applanated diameter, and a negligible change in surface curvature of the outer surfaces of the IOL.

Figure 11:
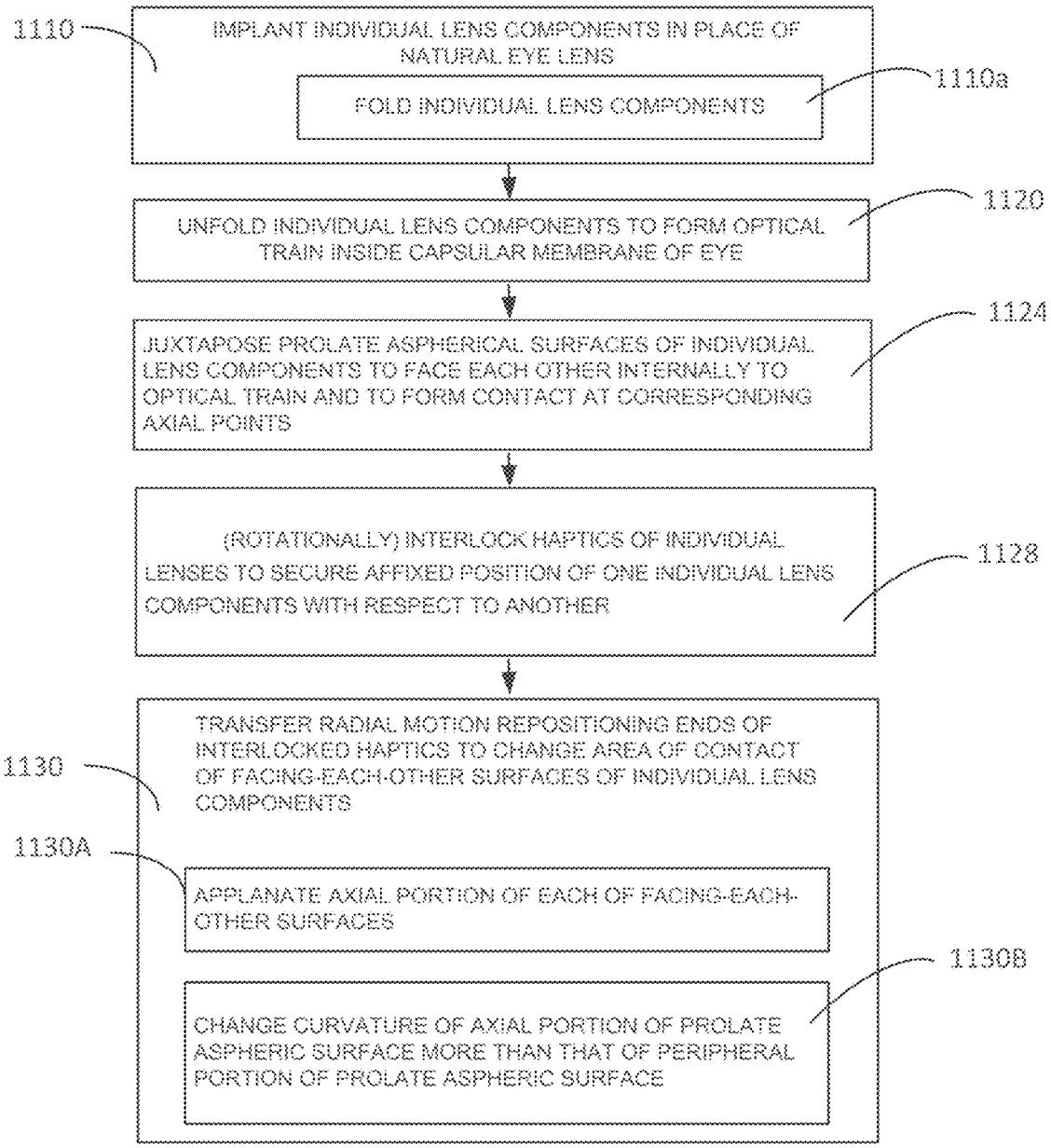
FIG. 11 is a flow-chart schematically depicting a method according to an embodiment of the invention.

In reference to FIG. 11, a flow-chart illustrating an embodiment of the method for vision correction is presented. The embodiment includes installing, in a required order, first and second individual lenses in a capsular membrane of an eye at step 1110. The implantation may optionally include folding the IOL, at step 1110A. It is appreciated that material composition of IOL embodiments of the invention allows the IOLs to be folded and inserted into the eye through a small incision (which make them a better choice for patients who have a history of uveitis and/or have diabetic retinopathy requiring vitrectomy with replacement by silicone oil or are at high risk of retinal detachment). At step 1120, the so inserted individual lenses are unfolded inside the eye such as to place each of the 2D-curved haptics of these lenses in mechanical cooperation with ciliary muscle of the eye.

The unfolding is followed by orienting the lenses in a capsule membrane of the natural lens of the eye such as to position the corresponding prolate aspherical surfaces of the first and second individual lenses to face each other, as step 1124. The posteriorly located individual lens that has an outer prolate aspheric surface facing the cornea is placed such as to be separated from the cornea by the anteriorly placed individual lens. Each of the first and second individual lenses has a set of haptics structured to be affixed to one another (optionally—via a rotational movement about an optical axis of one of the lenses) at step 1128 such as to form an IOL in which the individual lenses are in a physical contact at an axial point of the corresponding prolate aspheric surfaces and in which the haptic extension elements of one individual lens are passing through the locking notches of the receiving haptics of another individual lens while portions of these extension elements (including the ends of the extension elements) are rested in the interlocking grooves of the receiving haptics.

The formed IOL contains (i) a central optical portion that has an optical axis and that is formed by first and second optical elements that have respectively corresponding oblate aspheric surfaces in contact at their axial points and (ii) a set of flexible curved haptics, each of said haptics having proximal and distal sides, the proximal side being integrated with the central optical portion along a perimeter thereof. Either the step of unfolding or the step of interlocking may be accompanies with juxtaposing the flexible haptics and the posterior surface of the posteriorly positioned individual lens against an interior surface of a capsule membrane of a natural lens of the eye such as to place distal side of each of said haptics in mechanical cooperation with the capsule membrane.

Embodiment of the method may include step 1130, during which an area of contact between prolate aspheric surfaces, of the IOL, that are facing each other internally to the IOL is changed as a result of transmitting a force, applied to the interlocked haptics, centripetally to the equator of the IOL and transferring at least one of the equatorially and axially pressure formed by such force. The step of changing the area of contact is accompanied by applanation, 1130A, of these surfaces that is mutually-imposed on one another by the immediately adjacent individual lenses of the IOL on as a result of which a change of focal length of the IOL is realized. In particular, such change can be effectuated, at step 1130B, to a higher degree in the axial portion of the prolate aspheric surface than in a peripheral portion of such surface.

For the purposes of this disclosure and the appended claims, the use of the term "substantially" as applied to a specified characteristic or quality descriptor means "mostly", "mainly", "largely but not necessarily wholly the same" such as to reasonably denote language of approximation and describe the specified characteristic or descriptor so that its scope would be understood by a person of ordinary skill in the art. The use of this term neither implies nor provides any basis for indefiniteness and for adding a numerical limitation to the specified characteristic or descriptor. For example, a reference to a vector or line being substantially parallel to a reference line or plane is to be construed as such vector or line extending along a direction that is the same as or very close to that of the reference line or plane (for example, with angular deviations from the reference direction that are considered to be practically typical in the art). As another example, the use of the term "substantially flat" in reference to the specified surface implies that such surface may possess a degree of non-flatness and/or roughness that is sized and expressed as commonly understood by a skilled artizan in the specific situation at hand.

When integrated for operation, the IOL assembly sits within the existing lens capsule following cataract extraction, and is operable by mechanical axial compression and radial elongation created by the zonular tension (just as a natural lens works, with the same neurological feedback control actuation). Internal, facing each-other surfaces of the lens assembly mutually deform to change an overall optical power o the assembly and subsequently accommodate the assembly by concentrating both the force of existing capsular axial compression and radial elongation to small internal surface area which deforms to create the power change. Two or more interlocked-through-haptics mutually-deforming deforming lens elements, forming the assembly, effectively combine the total physiologic force available from axial compression and radial elongation. Lens elements can be inserted to the lens capsule separately and coupled (interlocked) internally.

Disclosed aspects, or portions of these aspects, may be combined in ways not listed above. Accordingly, the invention is not intended and should not be viewed as being limited to the disclosed embodiment(s), and certain modifications not changing the scope of die invention can be made. For example, and in reference to a specific embodiment depicted in FIGS. 1A and 1B, it is not necessary that the individual lens at the front (lens 126 in FIG. 1A) has haptic extension elements while the posterior individual lens (lens 128 in FIG. 1B) has haptics with responding locking notches and interlocking grooves: the types of haptics can be reversed such that it is the front lens component in the IOL system that has a haptic containing notches and grooves, while another individual lens component is equipped with corresponding haptic extension elements. Similarly, while (both) individual lenses on the IOL system of the invention have been depicted to lenses of positive optical power, the scope of the invention and the principle of operation of the invention does not change when at least one of the individual lenses of the overall IOL system is a lens with negative optical power.

Moreover, the scope of the invention is not limited to any specific shape of the lens. As non-limiting examples, either of biconvex, plano-convex, plano-concave, biconcave, positive meniscus, and negative meniscus lenses (optionally modified to provide for prolate asphericity of the mutually-deforming surfaces, as discussed above) can be employed to implement an embodiment of the invention, It is also appreciated that a different number of individual lenses (three or more, for example) can be used to form an interlocked embodiment of the IOL in a fashion similar to that disclosed above, the accommodation to a near-distance object in such IOL being effectuated at least partly due to the applanation of the mutually-deforming, facing each other surfaces of the immediately-adjacent individual lenslets.

Figure 13:
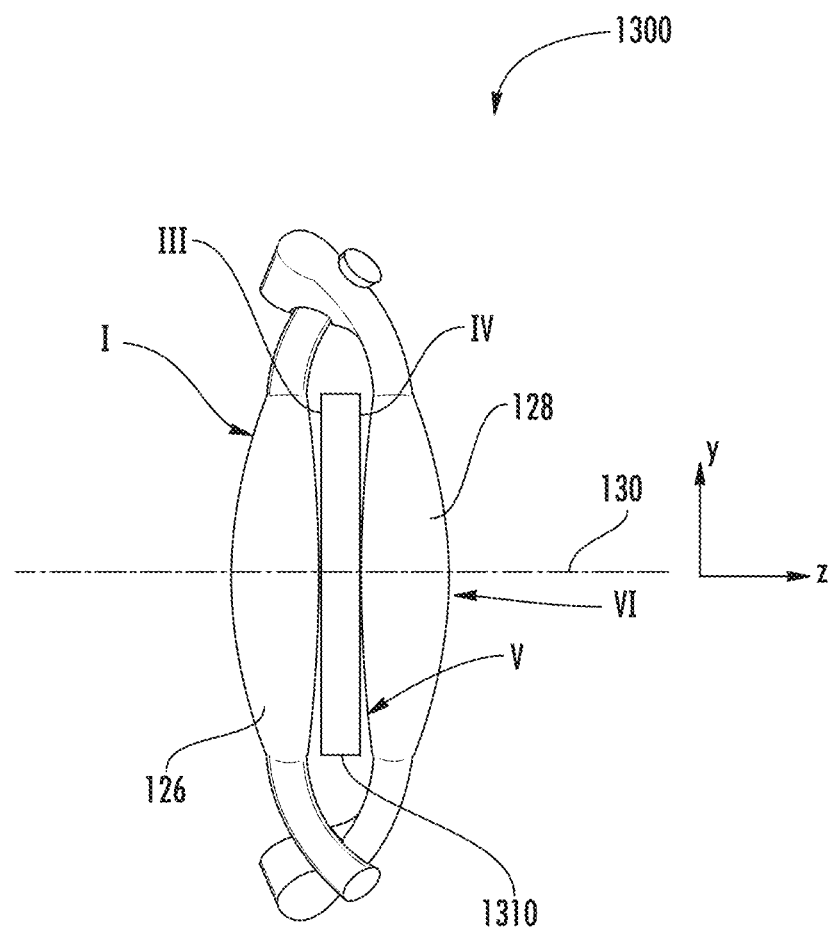
FIG. 13 is a schematic diagram of a related embodiment of the invention.

Alternatively, a train of optical elements from which the overall IOL system is formed may include an optical element possessing a substantially zero optical power. An example of one specific embodiment 1300, in which an element 1310 is positioned co-axially with and between the individual lens components 126, 128 is illustrated in FIG. 13, without the showing of optional corresponding haptic elements, for simplicity of illustration. In this structure, the optical surfaces are labeled sequentially, along the z-axis (a direction of propagation of light from an object), such that the anterior lenslet 126 has surfaces I, II; the element 1310 has surfaces III, IV; and the posterior lens 128 has surfaces V, VI. In this implementation, the element 1310 may be characterized by, for example, slightly negative optical power or optical power that is substantially zero, and be made from a soft material such as silicone or collamer material having a modulus of elasticity that is at least an order of magnitude smaller than that of neighboring lenslets (which, in turn, may have different moduli of elasticity as compared to one another). The moduli of elasticity for the various materials may range (hut not limited to) between about 1000 kPa and abut 1 kPa. These parameters are chosen to provide for a modulus of elasticity of the element 1310 that is lower than moduli of elasticity of the lenses 126, 128.

Furthermore, it is recognized that, generally, a given individual component or lenslet of the overall interlocked IOL system may, in a specific embodiment, have a complex structure such as, for example, one of those disclosed in U.S. patent application Ser. Nos. 14/193,301 and 14/195,345, the disclosure of which is incorporated herein by reference. As a non-limiting example and without loss of generality, an individual lens component of the present embodiment 200 can be structured to have an optical portion configured as gel-based lens discussed in Ser. No. 14/195,345 in reference to FIGS. 1A and 1B therein. In this case, an individual lens components may be structured as a lens having a (i) first rotationally symmetric optical portion with an optical axis and a focal length and defined by a first oblate aspheric surface and a deformable prolate aspheric surface, the optical portion operable to gradually change the focal length in response to deformation of the prolate aspheric surface; and (ii) first and second flexible haptic wings, each having proximal and distal sides, the proximal side being integrated with the first rotationally symmetric optical portion at least along a perimeter thereof, such that said lens is dimensioned to be placed, in operation, in mechanical cooperation with a ciliary body muscle of an eye of a subject such that, in response to tension applied to a at least one of zonules and capsular membrane of a natural lens of the eye by the ciliary body muscle, a curvature of the prolate aspheric surface is changed substantially without axial repositioning of said lens to cause a change in the focal length.

As another non-limiting example, an individual lens component of the present embodiment can be structured as a fluidic intraocular lens with flexible interior membrane discussed in Ser. No. 14/195,345 in reference to FIGS. 9A, 9B therein. In this case, an individual lens component may be structured as a lens comprising (i) a first rotationally symmetric optical portion having an optical axis and a first optical power, wherein a first volume of the first rotationally symmetric optical portion is defined by a posterior curved plate having a first perimeter and a flexible membrane, said first volume being filled with a first fluid having a first refractive index; (ii) a second rotationally-symmetric optical portion co-axial with the first rotationally symmetric portion and having a second optical power, wherein a second volume of said second rotationally symmetric optical portion is defined by an anterior rigid curved plate having a second perimeter and said flexible membrane, said second volume being filled with a second fluid having a second refractive index, such that the posterior and anterior plates being integrated with one another along said first and second perimeters and such that flexible membrane are sealingly affixed to at least one of said posterior and anterior plates at least one of the first and second perimeters such as to prevent dispensation of any of the first and second fluids from a respectively corresponding volume of the first and second volumes; and (iii) first and second flexible haptic wings, each having proximal and distal sides, the proximal side being integrated with at least the anterior plate at least along the first perimeter; said first and second optical portions being operable to gradually change at least one of the first and second optical powers in response to deformation of said membrane while the anterior and posterior plates substantially maintain their corresponding shapes.

Examples of Embodiments for Non-Ophthalmic Use.

FIGS. 14A, 14B, 15A, and 15B illustrate schematically in side and front views an embodiment 1400 of a variable-focus lens system structured and operable according to the idea of the invention. Here, the system 1400 is shown to include a train (array) of individual lenses 1410, 1420, 1430, 1440 disposed sequentially and co-axially about the axis 1450 within the housing 1460 that is equipped with an appropriate stopper element (not shown) at the front portion 1460A of the housing 1460 to keep the lenses within the hollow of the housing. The individual lenses are made, for example, from materials discussed above in reference to IOL-related embodiments of the invention. As shown, each two immediately adjacent lenses arc abutting one another at a corresponding axial point such that the mutually-facing surfaces of these two immediately adjacent lenses are in contact with one another at an axial point. For example, surfaces II, III of the system (respectively corresponding to lenses 1410, 1420) are in contact at an axial point C, while surfaces VI, VII of the system (respectively corresponding to lenses 1430, 1440) are in contact at an axial point S. Optionally, at least one of the surfaces in a pair of mutually-contacting surfaces of the lens system 1400 is a prolate aspheric surface. For example, at least one of surfaces II, III has a prolate aspheric profile about the axis 1450.

At the back portion of the housing 1460, an actuating piston 1470 is mated (as known in the art) such as to allow for application of pressure to the train of lenses as a result of movement of the piston 1470 along the axis 1450. FIGS. 14A and 14B illustrate the embodiment 1400 when the piston 1470 is in a neutral position defined by no interactive axial force between a lens of the system and the surface of the piston. Under these circumstances, as seen in the front view of FIG. 14B, there is substantially no applanation of any of the internal surfaces of the lens system. In operation (and in reference to FIGS. 15A, 15B), the piston 1470 is actuated along the axis 1450—for example, in the direction indicated by an arrow 1474 such at to apply axially-directed pressure to an individual lens of the system 1400. It is appreciated that, depending on a the piston 1470 can be specifically structured, as will be understood by a person of ordinary skill in the art, to apply pressure to either the outermost lens 1440 (thereby creating a force F directed along 1474 and axially-compressing the combination of lenses 1410, 1420, 1430, and 1440), or to another lens in the system. (In one specific implementation, for example, the piston 1470 can be structured to apply pressure to lens 1420, thereby axially compressing the lenses 1410 and 1420 such as to applanate the mutually-facing surfaces II, III.) In the general case, however, as shown in FIG. 15A, the piston 1470 compresses the whole train of lenses of the embodiment 140o by applying axial force to the lens 1440. As a result—and as a function of the strength of the axially-applied force cause by the movement of the piston 1470—the facing surfaces of the immediately-adjacent lenses mutually deform each other, as discussed above in reference to FIGS. 5A, 5B, forming axially-centered applanated areas 1480. A progression 1480A of such areas 1480 with radii $R_i$ increasing as a function of increasing force F is schematically shown in FIG. 15B. The applanation 1480 of the lens' surfaces is reversible and repeatable as a result of repositioning of the piston 1470 in an opposite direction. To this end, the lens material works as a spring reversing the actuation of the lens in proportion to reduction in actuation pressure at the piston 1470.

In one specific implementation, the housing 1460 is a cylindrical construction made of a rigid material (for example, metal) while the actuating cylinder of the piston 1470 is made of an optically clear material having a modulus of elasticity of more than 1,000 kPA (such as poly-methyl-methacrylate, PMMA, for example). The first lens 1410 in the series of lenses may be also made rigid with a high modulus of elasticity (such as that of PMMA). The remainder of the internal lenses (as shown, lenses 1420, 1430, and 1440) are constructed of a much softer material such as silicone, acrylic, or collamer having a modulus of elasticity within the range of 0.1 kPa to 100 kPa. The internal applanating surfaces are compressed between the rigid piston 1470 and rigid lens 1410. The internal opposing lens surfaces are applanated against each other thus progressively negating the optical power contribution of these surfaces to the overall lens system 1400 as the surfaces applanate over an increasing diameter, as shown in FIG. 15B. Optionally, the internal immediately adjacent opposing lens surfaces arc constructed in a prolate aspherical manner so that i) to increase the sphericity of such surface as a result of progressive applanation caused by the mechanical compression due to force F, beginning at the apex of a given surface; and ii) to minimize the discontinuity of spatial transition between the applanated portion of the surface (centered at the axis 1450) and the portion of the lens surface encircling such applanated area, and associated optical aberrations. The materials, thicknesses, and lens surface curvatures are judiciously chosen such that the progressive "stepped" or "staged" applantation of the serial surfaces approximates a spherical lens over the entire amplitude of lens power. In other words, at least one of the adjacent opposing lens surface in question is defined such that, during a process of increase in a diameter of die applanated area in response to increase of force F, optical aberrations of the overall optical system that are caused by changes in such diameter are minimized.

Figures 16A, 16B:
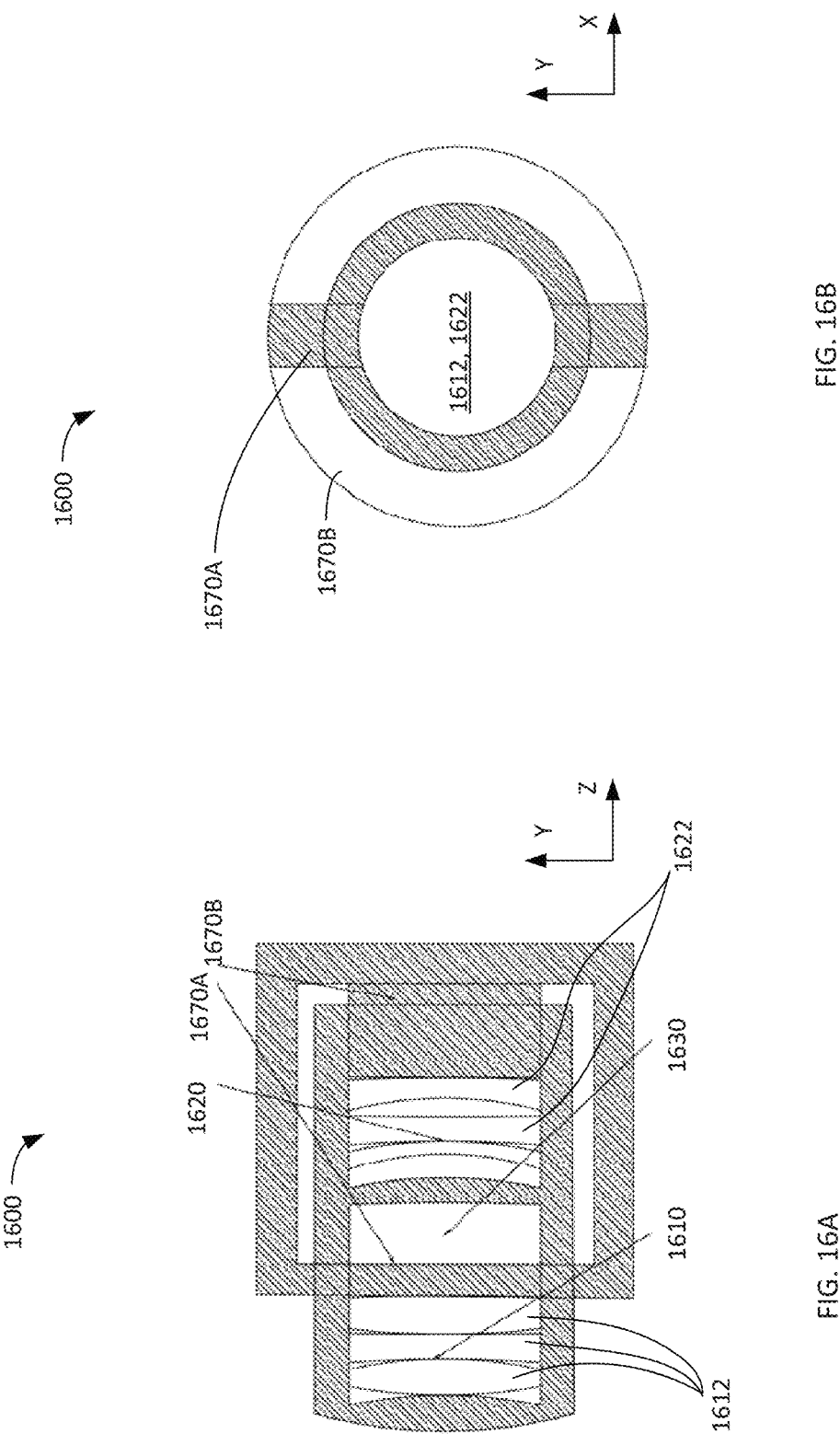
FIGS. 16A and 16B are diagrams illustrating, in side and front views, an embodiment of a variable-focus lens system including anterior sub-system and posterior subsystem the focal lengths of which are individually adjustable according to the embodiment of the invention.

FIGS. 16A, 16B illustrate a related embodiment 1600 structured to form a high-amplitude (from zero to about 20×) zoom lens. Specifically, the optical train of the system 1600 is for tied by an axially concatenated lens sub-systems 1610, 1620 such that the optical power of one subsystem has a sign that is opposite to that of the optical power of another sub-system. As shown in the example of embodiment 1600, the sub-system 1610 having an overall positive optical power includes a plurality of individual lenses 1612 at least two of which have surfaces contacting each other at an axial point in absence of axial pressure applied to such plurality of lenses. The sub-system 1620, on the other hand, is shown as a group of lenses 1622 possessing, aggregately and as a sub-system, negative optical power and separated with a gap 1630 from the sub-system 1620. At least two of the lenses 1622 have surfaces contacting each other at an axial point in absence of axial pressure applied to this group of lenses. In this embodiment, lenses in individual groups of lenses 1610, 1620 can be actuated such that actuation of one group of lenses is not connected with or affect the actuation of another group of lenses. For example, as shown, this can be achieved with structuring the means for applying axial pressure to the optical train of the system 1600 as a combination of two pistons 1670A and 1670B, operable individually and without interference with one another.

Figure 17:
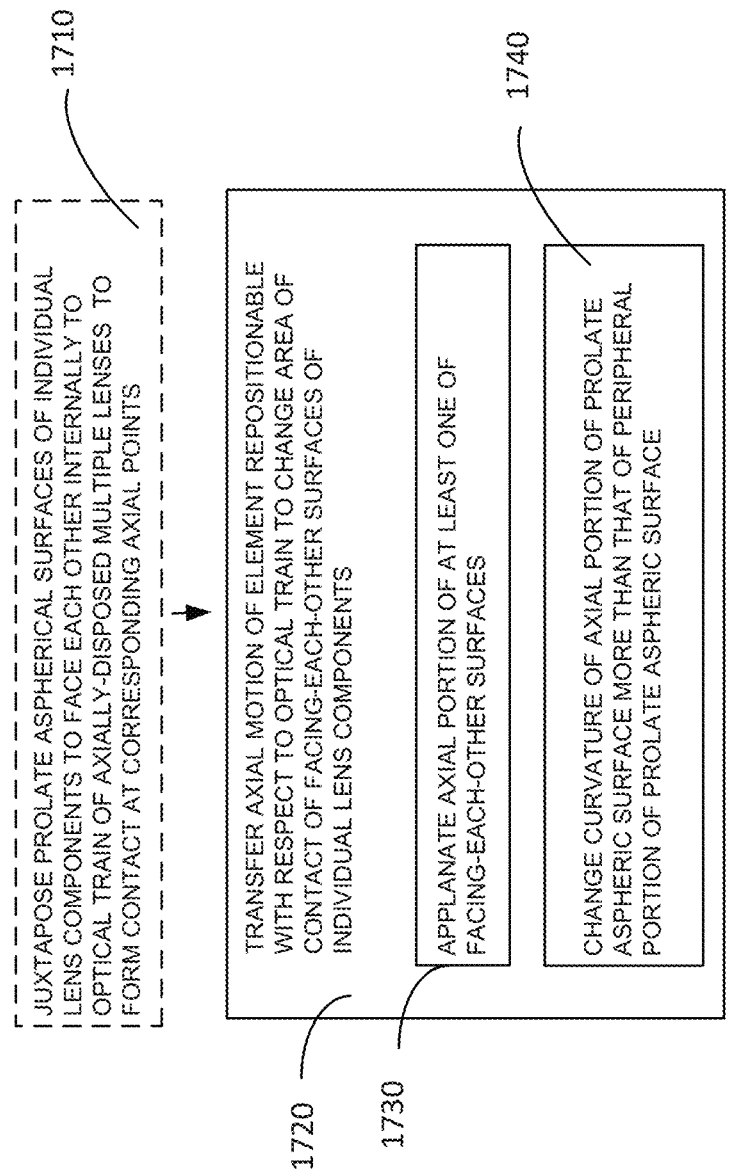
FIG. 17 is a flow-chart schematically depicting a method according to an embodiment of the invention.

Applanting variable-focus lens system structured according to embodiments 1400, 1600 are able to operate within the range of accommodation of optical power of about 60 diopters. Negating the optical power contribution provided by the six internal surfaces of the embodiment 1400 (surfaces II, III, IV, V, VI, and VII) by the staged applanation reduces the optical power of the lens system by about 60 diopters if each of these internal surfaces contributes, on average, of about 10 diopters of optical power to the overall optical power o the system 1400. The lens system requires minimal actuation force of a few grams and, in some implementations, about 100 microns of movement to maximize the range of the optical power. Such actuation may be implemented with either piezoelectric crystal or a conventional pressure actuator (not shown for simplicity of illustration). FIG. 17 provides a flow-chart of a method of operation of an embodiment of the invention. Here, the operation of the embodiment may be initiated by either compressing a group of individual lenses that have been already pre-assembled, at step 1710, into an optical train or, alternatively, by forming such assembly at step 1710 to begin with. At step 1720, a motion of an element of the lens-system harness directed along an optical axis of the lens system is transferred to a lens of the system to change area of contact of mutually-facing surface of the immediately adjacent lenses of the system causing, at step 1730, applanation of an axial portion of at least one of such surfaces. Optionally, at step 1740, when the so-applanated surface is a prolate aspherical surface, the curvature of the axial portion of the prolate aspherical surface can be change more than the curvature of the peripheral portion of the prolate aspherical surface (which encircles the axial portion). Other material and mechanical parameters of the system and motion/forces required to operate such system are similar to those discussed in reference to ophthalmological embodiments of the invention.

These and other modifications remain within the scope of the invention.

The invention claimed is:

1. A method for operating a pseudophakic lens assembly, the method comprising:
   juxtaposing first and second lenslets coaxially, such that a first surface of a first optical portion of the first lenslet and a second surface of a second optical portion of the second lenslet face each other,
      wherein at least one of said surfaces includes a prolate aspheric surface,
      wherein the first lenslet includes at least two first haptic portions, each having a proximal end integrated with a peripheral region of the first optical portion and a distal end; and
      wherein the second lenslet includes at least two second haptic portions respectively corresponding to the at least two first haptic portions,
   interlocking each of said at least two first haptic portions with the respectively corresponding at least two second haptic portions by rotating at least one of the first lenslet and the second lenslet with respect to the other of the first lenslet and the second lenslet about an axis so as
      to form a first lens assembly, in which the first lenslet and the second lenslet are securely affixed to one another and
      to define a point of contact between said facing each other surfaces of the first lenslet and the second lenslet in an unstressed state of the assembly; and
   varying a first area of contact between the first surface and the second surface that are facing each other in response to a radially-vectored force transferred to the first optical portion and the second optical portion through the at least two first and second haptic portions interlocked with one another.

2. A method according to claim 1, further comprising applanating at least a portion of at least one of the facing each other surfaces of the first and the second lenslets within said area of contact, and
   increasing said first area of contact by increasing a distance between distal ends of the at least two first haptic portions.

3. A method according to claim 1, further comprising inserting the first and the second lenslets individually into an eye through an incision in a cornea; and
   conforming a curvature of a posterior surface of the lens assembly to an internal surface of a natural lens capsule of the eye.

4. A method according to claim 3, wherein said juxtaposing and said interlocking are carried out after said inserting.

5. A method according to claim 1, further comprising changing an optical power of said pseudophakic lens assembly by causing the facing each other surfaces of the first lenslet and the second lenslet to mutually deform each other.

6. A method according to claim 5, wherein said changing the optical power includes changing a curvature of an axial portion of at least one of the facing each other surfaces of the first and the second lenslets by a first amount and changing a curvature of an annular portion of said at least one of the facing each other surfaces by a second amount, the annular portion circumscribing the axial portion, the first amount exceeding the second amount.

7. A method according to claim 1,
wherein said juxtaposing includes juxtaposing the first and the second lenslets, each lenslet having a prolate aspheric surface in the unstressed state, and
wherein said varying includes causing said prolate aspheric surfaces of the first and the second lenslets to apply force towards one another so as to mutually applanate each other.

8. A method according to claim 1, wherein said interlocking includes affixing a first region of the at least two first haptic portions in a notch of a respective second region of the at least two second haptic portions and a corresponding distal end of said first region of the at least two first haptic portions in a groove of the respective second region of the at least two second haptic portions, said groove being tangentially parallel to a perimeter of the first optical portion.

9. A method according to claim 1, further comprising
juxtaposing a third lenslet coaxially with said first lenslet and said second lenslet, wherein the third lenslet includes at least two third haptic portions;
interlocking each of said at least two third haptic portions with at least one of
(i) respectively corresponding region of the at least two first haptic portions, and
(ii) respectively corresponding region of the at least two second haptic portions;
by rotating at least one of said first lenslet, said second lenslet, and said third lenslet about the axis so as
to form a second lens assembly, in which the first lenslet, the second lenslet, and the third lenslet are securely affixed to one another and
to define a point of contact between a third surface of the third lenslet and a fourth surface of the at least one of the first and the second lenslets.

10. A method according to claim 9, further comprising changing a second area of contact between said third surface and said fourth surface in response to said radially-vectored force.

11. A method according to claim 10, wherein said changing includes causing at least one of the third surface and the fourth surface to apply force towards the other of the third surface and the fourth surface so as to applanate the at least one of the third surface and the fourth surface.

12. A method according to claim 9, wherein said juxtaposing the third lenslet includes juxtaposing the third lenslet in which the third surface in an unstressed state includes a prolate aspheric surface.

13. A method according to claim 9, wherein said juxtaposing the third lenslet includes juxtaposing the third lenslet that has zero optical power.

\* \* \* \* \*